(12) United States Patent
Itkowitz et al.

(10) Patent No.: US 11,622,672 B2
(45) Date of Patent: Apr. 11, 2023

(54) METHOD FOR POSITIONING AN ENDOSCOPE WITH FLEXIBLE SHAFT

(71) Applicant: Intuitive Surgical Operations, Inc., Sunnyvale, CA (US)

(72) Inventors: Brandon Itkowitz, San Jose, CA (US); Simon Peter DiMaio, San Carlos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1059 days.

(21) Appl. No.: 16/313,350

(22) PCT Filed: Jun. 26, 2017

(86) PCT No.: PCT/US2017/039264
§ 371 (c)(1),
(2) Date: Dec. 26, 2018

(87) PCT Pub. No.: WO2018/005354
PCT Pub. Date: Jan. 4, 2018

(65) Prior Publication Data
US 2019/0159661 A1 May 30, 2019

Related U.S. Application Data

(60) Provisional application No. 62/357,588, filed on Jul. 1, 2016.

(51) Int. Cl.
*A61B 1/00* (2006.01)
*A61B 90/50* (2016.01)
(Continued)

(52) U.S. Cl.
CPC ...... *A61B 1/00149* (2013.01); *A61B 1/00006* (2013.01); *A61B 1/05* (2013.01); *A61B 90/50* (2016.02); *A61B 2034/301* (2016.02)

(58) Field of Classification Search
CPC ............ A61B 1/00147; A61B 1/00149; A61B 1/00154; A61B 1/0016; A61B 1/00006;
(Continued)

(56) References Cited

U.S. PATENT DOCUMENTS

2009/0259097 A1 10/2009 Thompson
2011/0282359 A1* 11/2011 Duval ................. H01F 27/2823
606/130
(Continued)

FOREIGN PATENT DOCUMENTS

JP 2011212244 A 10/2011
WO WO-2005096961 A1 10/2005

OTHER PUBLICATIONS

International Search Report and Written Opinion for Application No. PCT/US2017/039264, dated Oct. 13, 2017, 18 pages.
(Continued)

*Primary Examiner* — Ryan N Henderson
*Assistant Examiner* — Pamela F Wu
(74) *Attorney, Agent, or Firm* — Fish & Richardson P.C.

(57) ABSTRACT

Systems and methods for endoscopic operations are described. For example, the disclosure provides mechanisms for sensing and controlling a field of view of an endoscope by determining a pose of the field of view using a first location and a second location, and controlling the pose of the field of view by moving at least one of: the first portion and the second portion. The first location is of a first portion of the endoscope and the second location is of a second portion of the endoscope. The endoscope comprises a flexible portion disposed between the first portion and the second portion. The first and second locations are defined by a configuration, relative to the endoscope, of an endoscope support and a cannula. The endoscope support configured to
(Continued)

support the endoscope. A shaft of the endoscope is configured to extend through the cannula.

24 Claims, 11 Drawing Sheets

(51) Int. Cl.
*A61B 1/05* (2006.01)
*A61B 34/30* (2016.01)

(58) Field of Classification Search
CPC . A61B 1/00131; A61B 1/00135; A61B 90/50; A61B 90/57; A61B 2090/5025; A61B 2090/571; A61B 2090/506; A61B 2090/508; A61B 2034/301–306
USPC .................................................. 600/114, 118
See application file for complete search history.

(56) References Cited

U.S. PATENT DOCUMENTS

| | | | |
|---|---|---|---|
| 2012/0184968 A1* | 7/2012 | Schena | A61B 34/37 606/130 |
| 2014/0296872 A1 | 10/2014 | Cooper et al. | |
| 2015/0045814 A1* | 2/2015 | Prisco | A61B 17/0218 606/130 |
| 2015/0297299 A1* | 10/2015 | Yeung | A61B 34/76 600/102 |
| 2016/0184032 A1* | 6/2016 | Romo | B25J 9/1682 901/46 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

METHOD FOR POSITIONING AN ENDOSCOPE WITH FLEXIBLE SHAFT

CROSS REFERENCE TO RELATED APPLICATIONS

This application claims the benefit of U.S. Provisional Application No. 62/357,588, filed Jul. 1, 2016. The disclosure of the prior application is considered part of and is incorporated by reference in the disclosure of this application.

TECHNICAL FIELD

This disclosure relates to systems and methods for positioning a surgical tool, such as an endoscope, by computer control.

BACKGROUND

Manipulators such as robotic arms are electro-mechanical devices that are usually controlled at least in part by a programmable controller. Manipulators include link elements connected by joints that rotate (rotary joints), or translate (prismatic joints), or both rotate and translate; this design allows for movement of the manipulator. In many cases, the manipulator includes or is configured to couple to an "end effector" capable of performing some useful task.

Non-medical and medical procedures sometimes use manipulators to aid in performing the procedure. For example, surgical procedures sometimes use these manipulators to aid in the surgical process. Manipulators can be used to allow an operator enhanced dexterity in implement manipulation. Additionally, manipulator systems may be configured to provide improved ergonomics, accuracy, and flexibility in performing procedures, when compared to the same procedures performed without use of manipulators.

SUMMARY

This disclosure provides systems and methods for endoscopic systems. For example, the disclosure provides mechanisms for holding a flexible endoscope, for identifying location information about the endoscope, and for manipulating the endoscope.

In one implementation, an endoscopic system comprises an endoscope configured to be supported by an endoscope support and a controller communicably coupled to the endoscope. The endoscope comprises a shaft configured to extend through a cannula, and an image capturer configured to capture an image from a field of view. The controller is configured to determine a first location of a first portion of the endoscope and a second location of a second portion of the endoscope, and to determine a pose of the field of view using the first location and the second location. The endoscope comprises a flexible portion disposed between the first portion and the second portion. The first and second locations are defined by a configuration, relative to the endoscope, of the endoscope support and the cannula.

Implementations can include some, none, or all of the following features. The controller is configured to determine the pose of the field of view using the first location and the second location by determining a pose of a distal end of the shaft based on the first and second locations, by determining a flexure of the shaft using the first and second locations, by using the first location, the second location, and a flexure of the shaft, by a combination thereof, or the like. The controller is configured to control the pose of the field of view by moving the first portion, by moving the second portion, or by moving both the first and second portions. The controller moves the first portion by moving the endoscope support and move the second portion by moving the cannula, or vice versa. The controller is configured to roll the field of view by rotating the endoscope support and causing rotation of the first portion, by rotating a cannula support configured to support the cannula and causing rotation of the second portion, etc. The controller is configured to change a yaw or a pitch of the field of view by changing a yaw or a pitch of the cannula. The controller is configured to control the pose of the field of view by moving the first portion in accordance with a first movement and moving the second portion in accordance with a second movement, where the first and second movements performed separately would roll the field of view, and where the first and second movements performed in combination would not roll the field of view. The controller is configured to control the pose of the field of view by actively driving a change in a flexure of the shaft. The controller drives the change in the flexure of the shaft by controlling a tension in a drive cable extending through the shaft. The controller determines the flexure of the shaft using the tension in the drive cable. The controller is configured to receive a command to move a proximal portion of the endoscope without changing a pose of a distal end of the shaft, determine a movement of at least one of the endoscope support and the cannula, where the movement would move the proximal portion of the endoscope without changing the pose of the distal end by moving at least one of the first and second portions, and drive motion of the at least one of the endoscope support and the cannula in accordance with the movement. The endoscope support comprises a mechanical brake configured to prevent the endoscope from moving. The endoscope support comprises a sensor configured to sense: a deflection of a joint of the endoscope support, a deflection of a link of the endoscope support, a force applied to the endoscope support, a combination thereof, or the like. The controller is configured to move the endoscope support in response to: determining that the deflection of the joint is past a joint deflection criterion, determining that the deflection of the link is past a link deflection criterion, determining that the force applied is past a force criterion, determining a combination thereof, or the like.

In one implementation, a method of controlling a field of view of an endoscope comprises determining a pose of the field of view using a first location and a second location, and controlling the pose of the field of view by moving the first portion, the second portion, or both the first and second portions. The first location is of a first portion of the endoscope and the second location is of a second portion of the endoscope. The endoscope comprises a flexible portion disposed between the first portion and the second portion. The first and second locations are defined by a configuration, relative to the endoscope, of an endoscope support and a cannula. The endoscope support configured to support the endoscope. The shaft of the endoscope is configured to extend through the cannula.

Implementations can include some, none, or all of the following features. Determining the pose of the field of view using the first location and the second location comprises determining a pose of a distal end of the shaft based on the first and second locations, determining a flexure of the shaft using the first and second locations, determining a combination thereof, or the like. Controlling the pose of the field of view comprises moving the first portion by moving the endoscope support, moving the second portion by moving the cannula, rolling the field of view by rotating the endoscope support and causing rotation of the first portion, changing a yaw or a pitch of the field of view by changing a yaw or a pitch of the cannula, moving the first portion and the second portion, a combination thereof, or the like. Moving the first portion and the second portion comprises moving the first portion in accordance with a first movement and moving the second portion in accordance with a second movement, where the first and second movements performed separately would roll the field of view, and where the first and second movements performed in combination would not roll the field of view. Moving the first portion and the second portion comprises moving the endoscope support and moving the cannula. The method further comprises controlling the pose of the field of view by actively driving a change in a flexure of the shaft. The method further comprises receiving a command to move a proximal portion of the endoscope without changing a pose of a distal end of the shaft, determining a movement of at least one of the endoscope support and the cannula, where the movement would move the proximal portion of the endoscope without changing the pose of the distal end by moving at least one of the first and second portions, and driving motion of the at least one of the endoscope support and the cannula in accordance with the movement. Controlling the pose of the field of view comprises moving at least one of the first portion and the second portion in response to: determining that a deflection the endoscope support is past a deflection criterion, determining that a force applied to the endoscope is past a force criterion, determining a combination thereof, or the like.

In one implementation, a non-transitory machine-readable medium comprising a plurality of machine-readable instructions is disclosed. The instructions, when executed by one or more hardware processors, are adapted to cause the one or more hardware processors to perform a method of controlling a field of view of an endoscope as disclosed herein. For example, in an embodiment, the method comprises determining a pose of the field of view using a first location and a second location, and controlling the pose of the field of view by moving at least one of: the first portion and the second portion. The first location is of a first portion of the endoscope and a second location is of a second portion of the endoscope. The endoscope comprises a flexible portion disposed between the first portion and the second portion. The first and second locations are defined by a configuration, relative to the endoscope, of an endoscope support and a cannula. The endoscope support configured to support the endoscope. A shaft of the endoscope is configured to extend through the cannula.

In one implementation, an endoscopic system includes an endoscope support configured to hold an endoscope. The endoscope includes a shaft and an image capturer positioned at a distal end of the shaft. The image capturer configured to capture an image. The system further includes a cannula support configured to hold a cannula. The system further includes a controller includes a processor and configured to determine a pose of a point of the endoscope based on a first location of a first point of the endoscope and based on a second location of a point of the cannula.

Implementations can include some, none, or all of the following features. The shaft includes a major axis. A portion of the shaft is flexible in a direction orthogonal to the major axis. The shaft is of sufficient stiffness to overcome friction of the cannula in a direction along the major axis and in roll about the major axis. To determine the pose of the first point of the endoscope, the controller is configured to determine a flexure of the shaft. The image capturer is configured to capture stereoscopic images. The endoscope support includes a spar and a carriage configured to move along the spar and to hold the endoscope. The spar is telescoping such that a shape of the spar changes as the carriage moves. The pose of the first point of the endoscope has a third location in a surgical space and a first orientation in the surgical space. The surgical space is a Cartesian space having an axis pointing toward a point within a patient. The first location is in an endoscope space having an origin location and an origin orientation relative to the endoscope. The second location is in a cannula space having an origin location and an origin orientation relative to the cannula. To determine the pose of the point of the endoscope, the controller is configured to transform the first location into the surgical space; and transform the second location into the surgical space. To transform the first location into the surgical space, the controller is configured to sense a pose of the endoscope. To transform the second location into the surgical space, the controller is configured to sense a pose of the cannula support. The controller is further configured to receive an input to change a view of the image capturer; and generate, using the pose, commands to move the distal end of the endoscope to change the view of the image capturer in accordance with the received input. The commands to move the distal end of the endoscope are configured to move a proximal end of the endoscope and to not move the cannula. To generate, using the pose, the commands to move the distal end of the endoscope, the controller is configured to determine a path that is free of collisions for the proximal end of the endoscope. A portion of the shaft is flexible. The commands to move the distal end of the endoscope include commands to move the flexible portion of the shaft through a passage of the cannula having a fixed curve. The controller is further configured to: receive an input to move a proximal end of the endoscope; and generate, using the pose, commands to move the proximal end of the endoscope. The input to move a proximal end of the endoscope is generated in response to user pushing the proximal end of the endoscope. The input to move the proximal end of the endoscope is generated in response to user manipulation of an element of the system other than the endoscope. To generate, using the pose, the commands to move the proximal end of the endoscope, the controller is configured to determine a path that is free of collisions for the proximal end of the endoscope. The cannula includes a second major axis. A portion of the shaft is flexible. The commands to move the proximal end of the endoscope include commands to flex the portion of the shaft. The controller is further configured to: receive an input to move the cannula; generate commands to move the cannula; and generate commands to move the endoscope with the cannula. The commands to move the endoscope with the cannula are configured to maintain a view of the image capturer. A single robotic arm controls the endoscope support and the cannula support. A first robotic arm controls the endoscope support and a second robotic arm controls the cannula support.

In one implementation, an endoscope includes a shaft having a distal end and a proximal end. The endoscope further includes an image capturer positioned at a distal end of the shaft, the image capturer configured to capture an image. The endoscope further includes a housing positioned at the proximal end of the shaft and including a control element, the housing configured to be coupled to an endoscope support. The shaft includes a flexible portion configured to flex in response to manipulation of the control element of the housing by the endoscope support.

Implementations can include some, none, or all of the following features. The flexible portion is configured to flex at least 45 degrees in response to manipulation of the control element of the housing by the endoscope support. The shaft forms a channel configured to transmit a fluid to the distal end of the shaft. The channels is configured to transmit gas of a sufficient pressure to cool the distal end of the endoscope. The endoscope further includes an illuminator positioned at the distal end of the shaft, the illuminator configured to illuminate an area captured as an image by the image capturer. The illuminator has an activation connection that traverses the shaft and terminates at the distal end. The activation connection is configured to be switchably engaged to activate the illuminator. The image capturer transmits the image (or images) over a data link including at least one of the group consisting of conductive wire, fiber optic media, and a wireless data link. The image capturer includes two viewports, and wherein the images are stereoscopic images.

Some or all of the embodiments described herein may provide one or more of the following advantages. In some implementations, control of the proximal end of a flexible endoscope can allow for more control of the area around the patient. The end of the endoscope may be moved to accommodate other tool or people that move into positions around the patient. The distal end of the endoscope can be held in place while the proximal end is moved. This can allow for a steady view from the endoscope while rearranging surgical tools. The distal end of the endoscope can be moved without moving the proximal end, allowing an operator to achieve a desired view without having to worry about a moving proximal end of the endoscope.

The details of one or more embodiments are set forth in the accompanying drawings and the description below. Other features, objects, and advantages will be apparent from the description and drawings, and from the claims.

BRIEF DESCRIPTION OF THE DRAWINGS

Like reference symbols in the various drawings indicate like elements.

DETAILED DESCRIPTION

Figure 1:
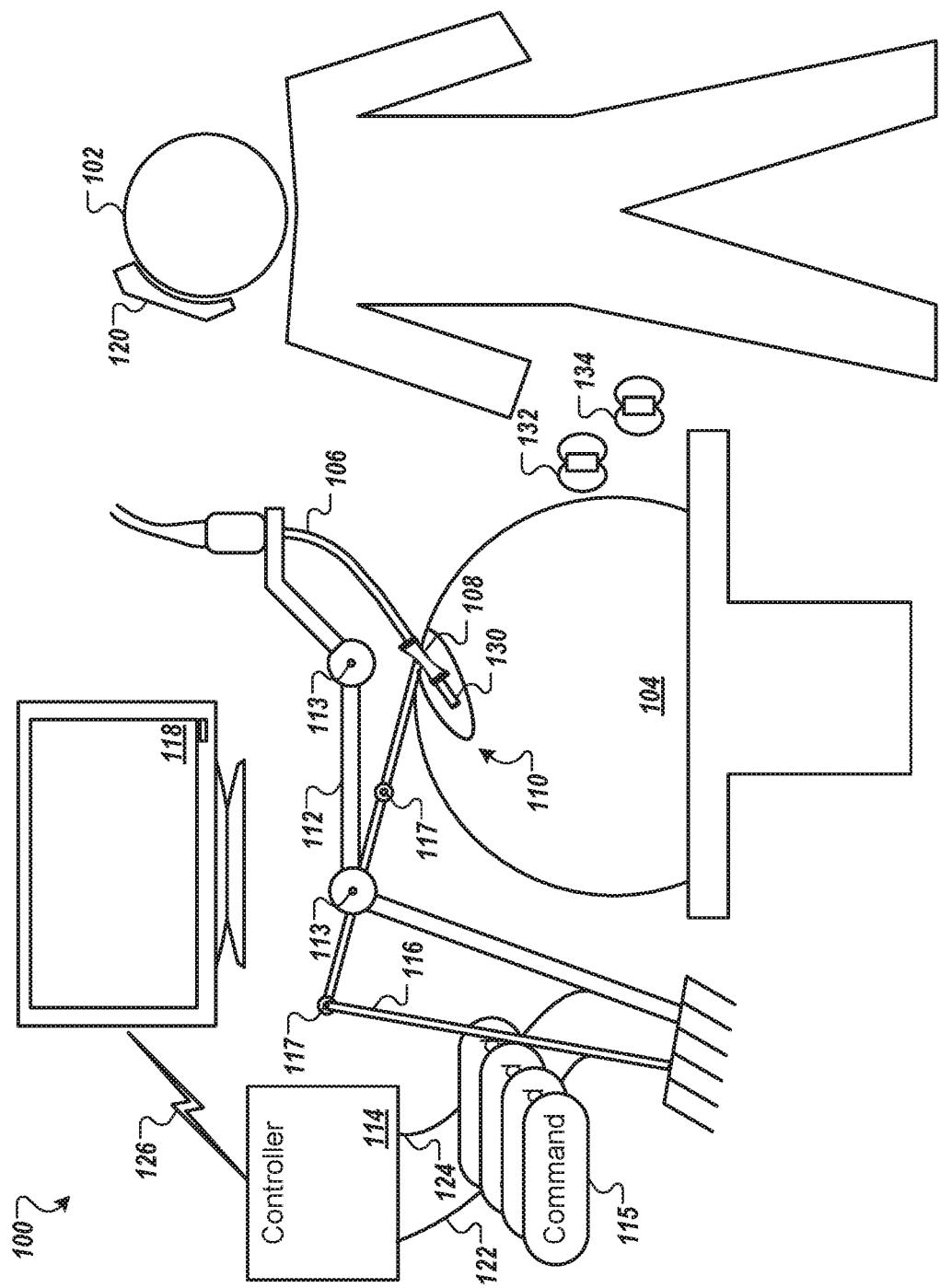
FIGS. 1-3 show schematic views of examples of endoscopic systems.

In various embodiments, one or more manipulators are configured to sense or define first and second locations. The first location is of a first portion of an image capturing device such as a flexible camera, and a second location of a second portion of the image capturing device. The first and second locations are used to determine a viewpoint of the image capturing device. The viewpoint of the image capturing device can be moved by moving the first location, the second location, a flexure of the image capturing device, a combination of thereof, or the like. This technique can be used to improve non-medical procedures such as inspection and repair using teleoperated systems. This technique can also be used to improve medical procedures such as those for medical diagnoses and treatment (including surgical and non-surgical procedures). In medical procedures, this technique can be used in a manner unrelated to actual treatment or diagnosis. For example, this technique can be used to move a proximal portion of the image capturing device to avoid collision with medical personnel while minimally changing or not changing the field of view.

In various embodiments, one or more manipulators are configured to hold a cannula and a flexible endoscope for use in medical operations such as medical diagnostic and treatment procedures (including surgical and non-surgical procedures). Unlike in some systems where the endoscope is rigid, a flexible endoscope can passively or actively flex and change shape during the procedure. This can provide the operator with more options in viewpoint control. This can also allow for movements of the proximal end of the endoscope while minimally changing, or without changing, the view of the endoscope. In order to properly support and control the flexible endoscope, a controller can determine the poses (i.e., positions and orientations) of points of the endoscope. The controller can then use these poses when generating commands to manipulate the endoscope.

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

Further, specific words chosen to describe one or more embodiments and optional elements or features are not intended to limit the invention. For example, spatially relative terms-such as "beneath", "below", "lower", "above", "upper", "proximal", "distal", and the like-may be used to describe one element's or feature's relationship to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various special device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. The words "including" or "having" mean including but not limited to.

It should be understood that although this description is made to be sufficiently clear, concise, and exact, scrupulous and exhaustive linguistic precision is not always possible or desirable, since the description should be kept to a reasonable length and skilled readers will understand background and associated technology. For example, considering a video signal, a skilled reader will understand that an oscilloscope described as displaying the signal does not display the signal itself but a representation of the signal, and that a video monitor described as displaying the signal does not display the signal itself but video information the signal carries.

In addition, the singular forms "a", "an", and "the" are intended to include the plural forms as well, unless the context indicates otherwise. And, the terms "comprises", "includes", "has", and the like specify the presence of stated features, steps, operations, elements, and/or components but do not preclude the presence or addition of one or more other features, steps, operations, elements, components, and/or groups. And, the or each of the one or more individual listed items should be considered optional unless otherwise stated, so that various combinations of items are described without an exhaustive list of each possible combination. The auxiliary verb may likewise implies that a feature, step, operation, element, or component is optional.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Elements described as coupled may be electrically or mechanically directly coupled, or they may be indirectly coupled via one or more intermediate components.

The term "flexible" in association with a part, such as a mechanical structure, component, or component assembly, should be broadly construed. In essence, the term means the part can be repeatedly bent and restored to an original shape without harm to the part. Many "rigid" objects have a slight inherent resilient "bendiness" due to material properties, although such objects are not considered "flexible" as the term is used herein. A flexible part may have infinite degrees of freedom (DOF's). Examples of such parts include closed, bendable tubes (made from, e.g., NITINOL, polymer, soft rubber, and the like), helical coil springs, etc. that can be bent into various simple or compound curves, often without significant cross-sectional deformation. Other flexible parts may approximate such an infinite-DOF part by using a series of closely spaced components that are similar to a snake-like arrangement of serial "vertebrae". In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. A short, flexible part may serve as, and be modeled as, a single mechanical constraint (joint) that provides one or more DOF's between two links in a kinematic chain, even though the flexible part itself may be a kinematic chain made of several coupled links. Knowledgeable persons will understand that a part's flexibility may be expressed in terms of its stiffness.

Unless otherwise stated in this description, a flexible part, such as a mechanical structure, component, or component assembly, may be either actively or passively flexible. An actively flexible part may be bent by using forces inherently associated with the part itself. For example, one or more tendons may be routed lengthwise along the part and offset from the part's longitudinal axis, so that tension on the one or more tendons causes the part or a portion of the part to bend. Other ways of actively bending an actively flexible part include, without limitation, the use of pneumatic or hydraulic power, gears, electroactive polymer (more generally, "artificial muscle"), other actuators or actuation systems, and the like. A passively flexible part is bent by using a force external to the part (e.g., an applied mechanical or electromagnetic force). A passively flexible part may remain in its bent shape until bent again, or it may have an inherent characteristic that tends to restore the part to an original shape. An example of a passively flexible part with inherent stiffness is a plastic rod or a resilient rubber tube. An actively flexible part, when not actuated by its inherently associated forces, may be passively flexible. A single part may be made of one or more actively and passively flexible parts in series.

A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller", encompasses both single-location and distributed implementations.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

FIG. 1 is a schematic view of an example of an endoscopic system 100 usable for procedures such as medical procedures (including surgical and non-surgical procedures). An operator 102 or multiple operators can perform procedures on a patient 104 aided by the endoscopic system 100. The endoscopic system 100 includes a flexible endoscope 106 that can pass through an access site to capture images from a workspace 110 in the patient 104. In the example shown in FIG. 1, a cannula 108 is inserted through the access site, and the flexible endoscope 106 passes through the access site by passing through a channel of the cannula 108. Where the procedure performed is a surgical procedure, the workspace 110 generally comprises a surgical area accessed for the surgical procedure.

In this example endoscopic system 100, the proximal end (i.e., the end near the operator 102 and away from the patient 104) of the flexible endoscope 106 is shown flexed. This allows for the better control of the space around the patient 104, giving the operator 104 a more ergonomic working environment or more options for the placement of other surgical equipment. The distal end (i.e., the end away from the operator 102 and near or in the patient 104) may be flexible as well. This can allow movement of the view from the flexible endoscope 106 without needing to move the proximal end of the flexible endoscope 106. This can also allow changes to the flexible endoscope's 106 point of view (orientation of the viewpoint, which is also called the "field of view") with reduced or eliminated impact on other surgical implements passing through the cannula.

An endoscope support 112 holds the flexible endoscope 106. The endoscope support 112 shown here comprises a manipulator (also called "robotic manipulator" or "robotic arm") that has a series of links that may be actuated to move the proximal end of the flexible endoscope 106. Additionally, the endoscope support 112 can include sensors 113 that sense information about the manipulator. For example, each sensor 113 can sense the angle between adjacent links. These sensors 113 can pass data from their sensing to a controller 114 to allow the controller 114 to calculate the state of the endoscopic support 112. The controller 114 can use this state information of the endoscope support 112 to determine where in space the endoscope support 112 is holding the flexible endoscope 106, as well as other information, such as the orientation with which the endoscope support 112 is holding the endoscope 106, the forces experienced by different parts of the manipulator comprising the endoscope support 112, the internal configuration of the endoscope support 112, etc.

A cannula support 116 holds the cannula 108. The cannula support 116 shown here comprises another manipulator (also called "robotic manipulator" or "robotic arm") that has another series of links that may be actuated to move the cannula 108. Additionally, the cannula support 116 can include sensors 117 that sense information about the manipulator. For example, the sensors 117 can sense the angle between adjacent links of the manipulator. This can include data passed to controller 114 that allows the controller 114 to calculate the state of the cannula support 116. The controller 114 can use this state information of the cannula support 116 to determine where in space the cannula support 116 is holding the cannula 108, as well as other information, such as the orientation with which the cannula support 116 is holding the cannula 108, the forces experienced by different parts of the manipulator comprising the cannula support 116, the internal configuration of the cannula support 116, etc.

The cannula support 116 and the endoscope support 112 in this example are shown schematically mounted to a same mechanical ground. This can include situations in which the cannula support 116 and the endoscope support 112 share the same base and situations in which the cannula support 116 and the endoscope support have different bases. For example, the cannula support 116 may be mounted to a rail of an operating table to move with the patient 104 while the endoscope support 112 may be mounted to a mobile cart. In another example, both the endoscope support 112 and the cannula support 116 may be mounted to a wall or a ceiling.

The controller 114 comprises computing hardware such as one or more hardware processors and memory, and is configured to receive, process, and transmit data of the endoscopic system 100. The memory non-transitory machine-readable medium comprising a plurality of machine-readable instructions which, when executed by the one or more hardware processors are adapted to cause the one or more hardware processors to perform a method such as those described herein. The controller 114 can send and receive data from sensors sensing information about the flexible endoscope 106, the endoscope support 112, the cannula 108, the cannula support 116, input devices 132 and 134, and from other sources. Examples of data that the controller 114 can receive include information from the sensors 113 and 117, image or video data from the flexible endoscope 106, and input signals from the input device 132. Examples of data that the controller 114 can send include commands 115 to actuate the endoscope support 112 and move part or all of the endoscope support 112, commands 115 to actuate the cannula support 116 and move part or all of the cannula support 116, commands 115 to control the flexible endoscope 106, and image or video data to be displayed on a monitor 118 or stereoscopic display 120. The controller 114 may communicate with other elements of the endoscopic system 100 via one or more data networks. These networks may include a conductive-wire datalink 122, a fiber-optic data link 124, wireless datalink 126, or other technologically appropriate datalinks.

The flexible endoscope 106 includes an image capturer 130 positioned at the distal end of the shaft of the flexible endoscope 106. This image capturer 130 can collect energy such as light, ultrasound, sound, RF, X-ray, heat, or some other energy type or combination of energy types to capture images. These images may be passed to the controller 114 for processing and display to the operator 102. When inserted through the cannula 108 into the workspace 110, the image capturer 130 can thus provide the operator 102 with a view into the workspace 110.

The flexible endoscope 106 may also include structures to assist in this image capturing. In some examples, the image capturer 130 can include an illumination source such as one or more light emitting diode (LEDs) to provide illumination in the visible or non-visible spectrum. In some examples, the flexible endoscope can include a gas passage to allow compressed gas to be delivered to insufflate the workspace 110 and/or to cool the image capturer 130.

The image capturer 130 can include an energy sensor to gather the energy needed to capture images. Light sensors such as charged-coupled devices (CCD) or complementary metal-oxide-semiconductor (CMOS) sensors, to name only two, can be used to collect light used to capture visual images. Thermal sensors such as forward looking infrared (FLIR) sensors, to name only one, can be used to collect infrared energy to capture heat images. Other types of sensors can be used to collect other types of energy, such as ultrasonic sensors can be used to collect ultrasonic energy.

The image capturer 130 may have one viewport, or may have multiple viewports. Image capturers 130 with two viewports may be configured to collect stereoscopic images. These stereoscopic images are created to mimic the binocular vision of the operator 102. When presented to the operator 102 in the stereoscopic display 120, the stereoscopic image can provide the operator 102 with a sense of depth information. In the stereoscopic display 120, a left-side view is presented to the operator's 102 left eye and a right-side view is presented to the operator's 102 right eye. In instances where the image capturer 130 captures a stereoscopic image, one of the two views, or a synthetic combination, can be presented by the monitor 118.

The operator 102 may use an input device 132 to generate input to change a view of the image capturer 130. For example, the operator 102 may use one or both hands to manipulate a part of the physical structure of the input device 132. This can include manipulating a joystick, moving a location-tracked target, or pressing a button. In response to being manipulated by the operator 102, the input device 132 can generate an input signal corresponding to the manipulation, and pass that input signal to the controller 114. The controller 114 can receive the input signals, and, if appropriate, send commands to other elements of the endoscopic system 100. For example, if the operator 102 manipulates the input device 132 to change the view of the image capturer 130, the controller 114 can generate commands to move the distal end of the flexible endoscope 106. These commands may include commands to flex the flexible endoscope 106 and/or commands to move the endoscope support 112 without moving the cannula 108. Holding the cannula 108 in place with these commands is desired in many cases. The cannula 108 is inserted into the patient 104 via an incision, and movement by the cannula 108 can lead to injury or other complications.

The endoscopic system 100 may also be configured to move the proximal end of the flexible endoscope 106 in response to operator 102 manipulation. For example, the operator 102 may manipulate the same input device 132 or another input device 134 to indicate a desire for the proximal end of the flexible endoscope 106 to move. Additionally or alternatively, the operator 102 may push the flexible endoscope 106, the endoscope support 112, or another element of the endoscopic system 100. This manipulation may result in input signals generated and passed to the controller 114. In response, the controller 114 can generate commands to move the proximal end of the flexible endoscope 106. These commands may include commands to flex the flexible endoscope 106 and/or commands to move the endoscope support 112 with or without moving the cannula 108.

In some cases, the flexible endoscope 106 can telescope, and these commands may include commands to extend or retract the flexible endoscope 106 (such as commands to extend or retract a shaft of the flexible endoscope 106) with or without moving the endoscope support 112 or the cannula 108, or changing a flexure of the flexible endoscope 106. As a specific example, these commands can include commands to rotate and translate the endoscope support 112 to move the proximal end of the flexible endoscope 106 while changing the length of the flexible endoscope 106, such that the resulting torsion on the flexible endoscope 106 from interactions with the endoscope support 112 and the cannula support 116, coupled with the change in length of the flexible endoscope 106, results in little or no change in the pose of a field of view of the flexible endoscope 106.

Thus, in some embodiments, the controller 114 is configured to receive a command to move a proximal portion of the endoscope 106 without changing a pose of a distal end of a shaft of the endoscope 106 (such as without changing a pose of the field of view of the image capturer 130). The controller 114 is further configured to determine a movement of the endoscope support 112, of the cannula 108, or of both the endoscope support 112 and the cannula 108, where this movement would move the proximal portion of the endoscope 106 without changing the pose of the distal end. The movement results in motion of at least one of the first and second portions of the endoscope 106. The controller is further configured to drive motion of the at least one of the endoscope support 112 and the cannula 108 in accordance with the movement.

In some cases, the operator 102 does wish to move the cannula 108. For example, when initiating and ending the medical procedure, the operator 102 can seat the cannula 108. The operator 102 can manipulate one or both of the input devices 132 and 134, or other elements of the endoscopic system 100. These manipulations can result in input signals to move the cannula 108, the input signals being passed to the controller 114. In response, the controller 114 can generate commands to move the cannula 108, optionally with movement of part or all of the flexible endoscope 106.

Although referred to here as an operator for simplicity, the operator 102 can represent any person that uses or is aided by the endoscopic system 100. Example titles of the people that may be represented by the operator 102 include, but are not limited to, doctor, surgeon, anesthesiologist, nurse, assistant, operator, user, and physician. Similarly, the patient 104 may be referred to other titles such as subject, etc. In some examples, the patient 104 is an artificial, anatomic model, or a part or all of a cadaver.

Thus, in various embodiments, the endoscopic system 100 comprises the endoscope 106 configured to be supported by the endoscope support 112. The endoscope 106 comprises a shaft configured to extend through the cannula 108, and the image capturer 130 configured to capture an image from a field of view. The endoscopic system 100 also comprises the controller 114 communicably coupled to the endoscope 106. The controller 114 is configured to determine a first location of a first portion of the endoscope 106 and a second location of a second portion of the endoscope 106. The endoscope 106 is flexible in that it comprises a flexible portion disposed between the first portion and the second portion. The first and second locations are defined by a configuration, relative to the endoscope, of the endoscope support 112 and the cannula 108. In some embodiments, the first portion is a portion of the endoscope 106 contacting or gripped by the endoscope support 112, and the second portion is be a portion of the endoscope 106 contacting or surrounded by the cannula 108. In other embodiments, the first and second portions are offset from but kinematically linked to the portion of the endoscope 106 contacting or gripped by the endoscope support 112 and contacting or surrounded by the cannula 108.

In some embodiments, the controller 114 is configured to determine the pose of the field of view by determining a pose of a distal end of a shaft of the endoscope 106 based on the first and second locations. In some embodiments, the controller 114 is configured to determine the pose of the field of view by determining a flexure of the shaft using the first and second locations. In some embodiments, the controller 114 is configured to determine the pose of the field of view by using the first location, the second location, and a flexure of the shaft. In some embodiments, the controller 114 is configured to determine the pose of the field of view by using a combination of the foregoing, or by using another technique involving the first and second locations, and involving information about the endoscope configuration derived from kinematic modeling, from sensor data, or from a combination thereof. Techniques for determination of the pose of the field of view, is discussed in more detail below, including in connection with FIG. 6.

In various embodiments, the controller 114 is configured to control the pose of the field of view by moving the first portion and not moving the second portion, by moving the second portion and not moving the first portion, or by moving both the first and second portions. The controller 114 may move the first portion through translation, rotation, or a combination of translation or rotation. For example, the controller 114 may move the first portion by translating the first portion though three-dimensional space, by rotating the first portion in yaw, pitch, or roll, or by any combination of translation and/or rotational movements. Similarly, the controller 114 may move the second portion through translation, rotation, or a combination of translation or rotation.

In some embodiments, the controller 114 moves the first portion by moving the endoscope support 112 and moves the second portion by moving the cannula 108, or vice versa. In some embodiments, the controller 114 is configured to roll the field of view of the image capturer 130 by rotating the endoscope support 112 and causing rotation of the first portion, by rotating a cannula support 116 configured to support the cannula 108 and causing rotation of the second portion, by a combination of these movements of these rotations, etc. In some embodiments, the controller 114 is configured to change a yaw or a pitch of the field of view by changing a yaw or a pitch of the cannula 108 (such as by changing a yaw or pitch of the cannula support 116).

In some embodiments, the controller 114 is configured to control the pose of the field of view by moving the first portion in accordance with a first movement and moving the second portion in accordance with a second movement. The first and second movements performed separately would roll the field of view, but the first and second movements performed in combination would not roll the field of view (that is, does not finally result in a roll of the field of view). In this way, the first and second movements counteract each other, and allow movement of a part of the endoscope 106 while minimally or not affecting the field of view. For example, the first movement may roll the field of view of the endoscope 106 by +30 degrees relative to a shaft axis of the endoscope 106, and the second movement may roll the field of view of the endoscope 106 by −30 degrees relative to the shaft axis. Together, these +30 and −30 degree movements cancel each other out sufficiently to provide little or no human-perceptible change to the field of view.

In some embodiments, the flexure of the endoscope 106 can be actively driven, and the endoscope 106 is not merely passively flexible. In such embodiments, the controller 114 can be configured to control the pose of the field of view by actively driving a change in a flexure of the shaft of the endoscope 106. As a specific example, some implementations of the endoscope 106 comprise a plurality of drive cables (perhaps configured in the form of tendons) through a shaft of the endoscope 106. The controller 114 drives the change in the flexure of the shaft by controlling a tension in one or more of the plurality of drive cables extending through the shaft. In such an embodiment, the controller 114 can be configured to determine the flexure of the shaft using the tension in one, some, or all of the plurality of drive cable and a mechanical model of the endoscope shaft. Addition discussion regarding cable control of endoscope flexure is below, including in conjunction with FIG. 5.

In some embodiments, the endoscope support 112 comprises a mechanical brake that prevents the endoscope 106 from moving when braked.

In some embodiments, the endoscope support 112 comprises a sensor or a plurality of sensors configured to sense: a deflection of one or more joints of the endoscope support 112, a deflection of one or more links of the endoscope support 112, a force applied to the endoscope support 112, a combination thereof, or the like. The controller 114 is configured to receive data from this sensor or plurality of sensors, and to move the endoscope support 112 in response to: determining that the deflection of the one or more joints of the endoscope support 112 is past a joint deflection criterion, determining that the deflection of the one or more links of the endoscope support 112 is past a link deflection criterion, determining that the force applied to the endoscope support 112 is past a force criterion, determining a combination of the foregoing has occurred, or the like.

Techniques for effecting the determination of the pose of the field of view, and for control of the endoscope 106 by the controller 114 is discussed in more detail below, including in connection with FIGS. 4-10.

Figure 2:
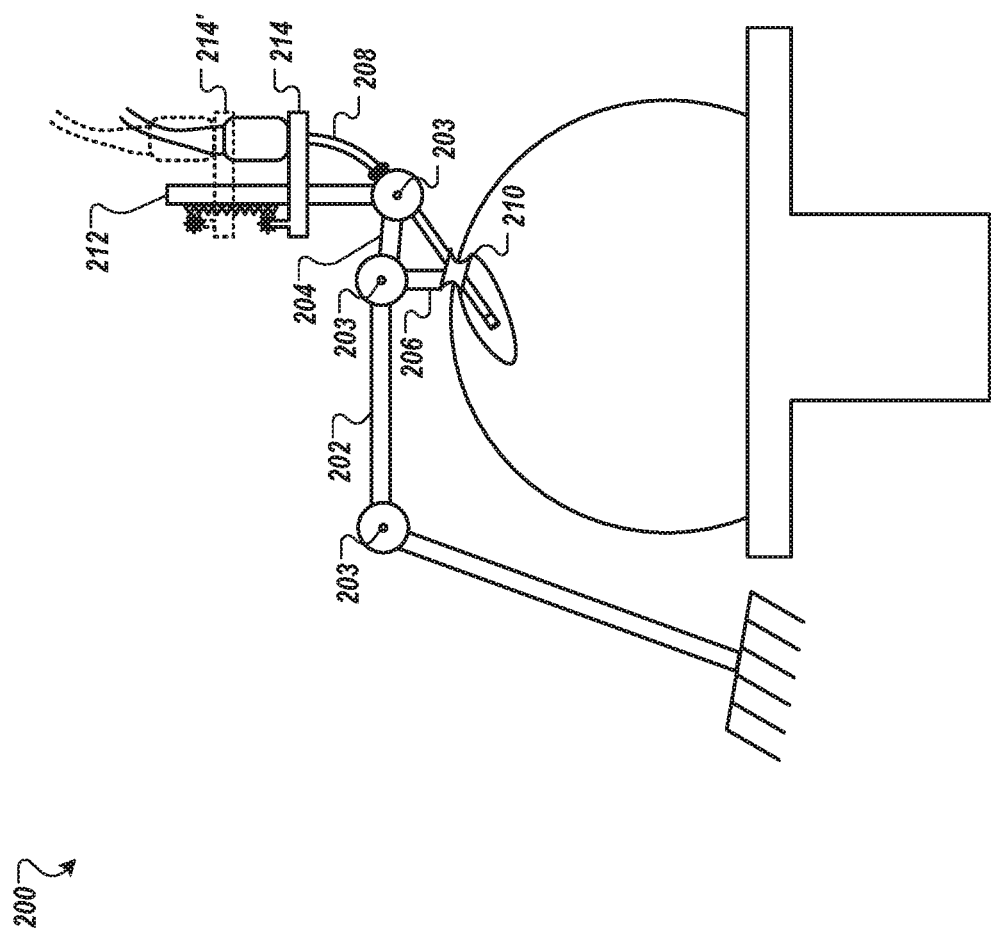
Figure 3:
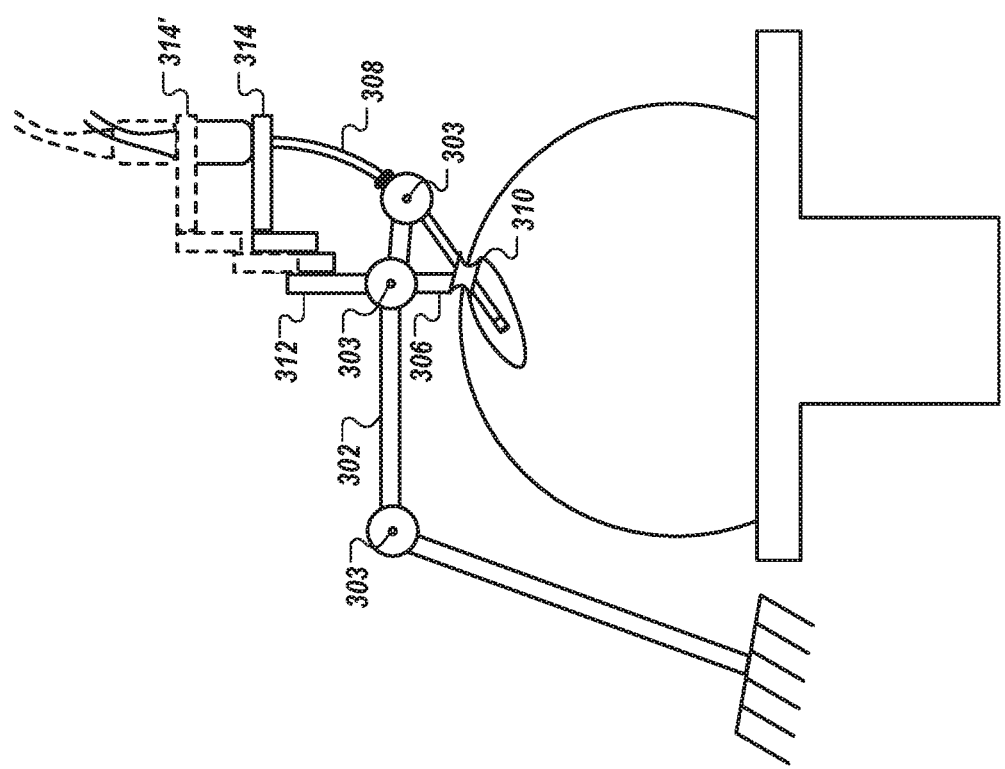

FIGS. 2 and 3 show schematic views of examples of other endoscopic systems 200 and 300 that may be used in procedures such as medical procedures (including surgical and non-surgical procedures). The endoscopic systems 200 and 300 show alternative configurations for elements such as cannula supports and endoscope supports. For clarity, some of the elements from the endoscopic system 100 are not shown. However, in various embodiments, the endoscopic systems 200 and 300 include elements shown in the endoscopic system 100, or other similar elements, and may be operated in a similar manner as discussed in conjunction with the endoscopic system 100. For example, the controllers for the endoscopic systems 200 and 300 may have the same or analogous functions to controller 114 for sensing and receiving data related to endoscope supports, cannulas, and endoscopes, for determining a pose of an endoscopic field of view, for control of the pose of the field of view, and the like.

Referring now to FIG. 2, a single robotic arm 202 (also "manipulator 202" or "robotic arm 202") includes both an endoscope support 204 and a cannula support 206. The cannula 210 shown in FIG. 2 is shorter than the cannula 108 shown for the endoscopic system 100, and thus contact and guide a shorter portion of the associated endoscope. The cannulas 108 and 210 may be used with either endoscopic system 100, 200, and are shown here separately in FIGS. 1 and 2 to illustrate that cannulas may be of any appropriate dimension and design. Sensors 203 sense information about the robotic arm 202 and pass data from their sensing to a controller. The controller may be similar to the controller 114. This controller can then calculate the state of the robotic arm 202. From this state data of the robotic arm 202, this controller can calculate the states of the endoscope support 204, of cannula support 206, or of both. Further, this controller can, by extension to calculations of the states of the endoscope support 204 or cannula support 206, calculate locations of parts or all of an attached endoscope 208, cannula 210, or both endoscope 208 and cannula 201.

In this example, the endoscope support 204 includes a spar 212 and a carriage 214. The interface between the spar 212 and the carriage 214 includes a drive mechanism, shown here as a sprocket and track. When engaged, the drive mechanism allows the carriage 214 to move along the spar to location 214' while holding the endoscope 208. This movement may be used, for example, to insert or retract the endoscope 208 in the cannula 210.

When an operator commands the viewpoint (also "field of view") of the endoscope to move, the image capturer of the endoscope 208 may need to move further into or out of the cannula 210. For example, a zooming in command will often involve causing the image capturer of endoscope 208 to move in the distal direction, and a zooming out command will often involve causing the image capturer of endoscope 208 to move in a proximal direction. In this example, the image capturer of endoscope 208 is located in the distal end of endoscope 208. To move the endoscope 208 distally, the carriage 214 can rotate the sprocket counter-clockwise from the view of FIG. 2. This rotation can move the carriage 214 down, pushing on the endoscope 208 distally. Conversely, by rotating the sprocket clockwise, the carriage 214 can move up, pulling the endoscope proximally.

Referring now to FIG. 3, a single robotic arm 302 (also "manipulator 302" or "robotic manipulator 302") includes sensors 303 and both an endoscope support 304 for holding an endoscope 308 and a cannula support 306 for holding a cannula 310.

In this example, the endoscope support 304 includes a telescoping spar 312 and carriage 314. The telescoping spar 312 can telescope to move the carriage 314 to location 314'. Doing so moves the endoscope 308 proximally and distally. In doing so, the telescoping spar 312 spar changes shape, expanding and contracting. By telescoping, the telescoping spar 312 reduces the sweep volume external to the patient as the viewpoint is moved. The endoscope 308 works in concert with the telescoping spar 312 to both reduce this sweep volume and to redirect it vertically from the view of FIG. 3. This can allow an operator to move themselves or other equipment into the space proximal to the cannula 310. If the endoscope 308 was not flexible, this space would normally be taken up by the proximal end of the endoscope.

Figure 4:
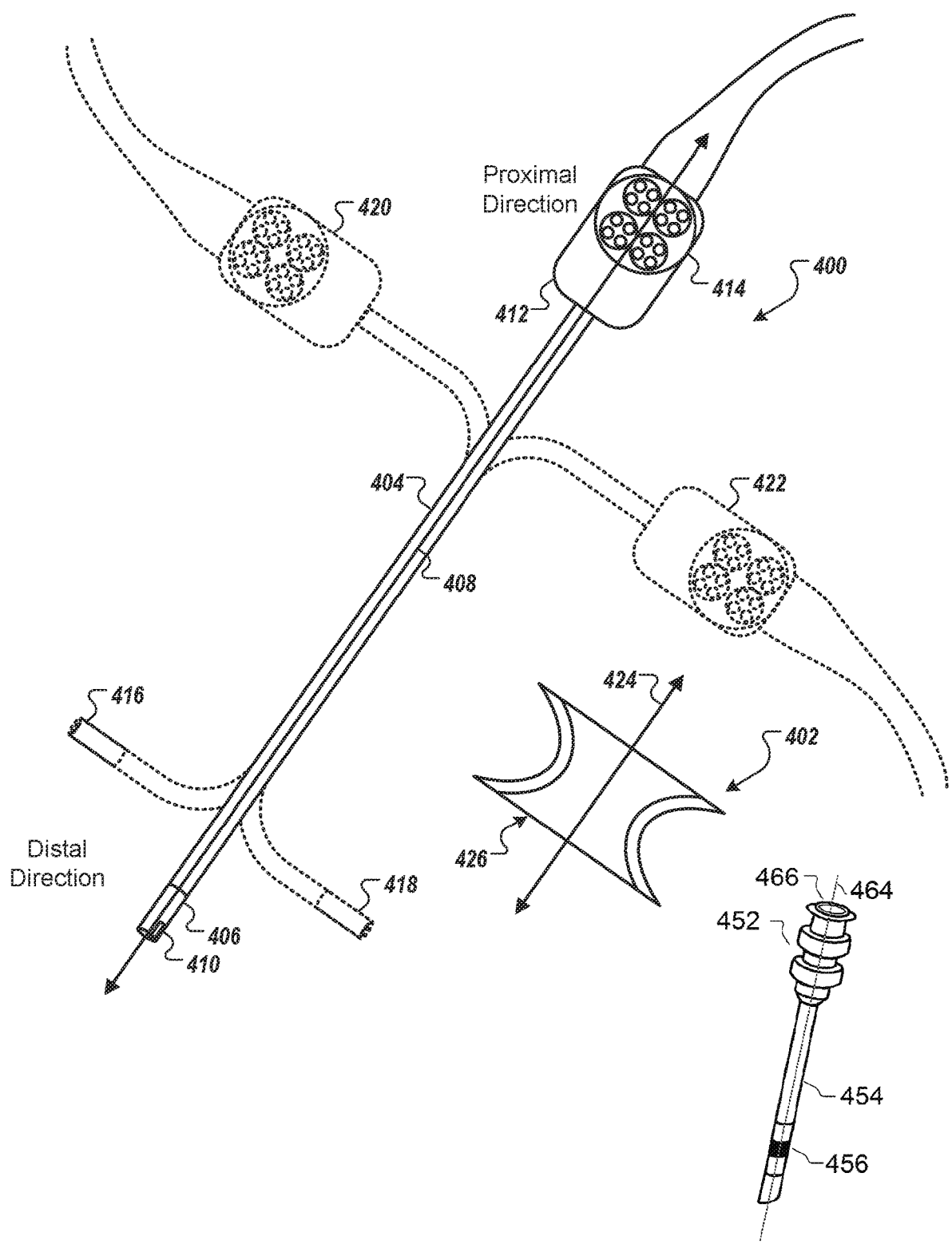
FIG. 4 shows a flexible endoscope and cannula that may be used for an endoscopic procedure.

FIG. 4 shows a flexible endoscope 400 and a cannula 402 that may be used for endoscopic procedures. The flexible endoscope 400 and cannula 402 may be used, for example, in the endoscopic systems 100, 200 and 300, or in other systems. The cannula 402 is shown here in a cross-sectional view, and a cross-section of the walls of the cannula 402 surround a passage 426.

The endoscope 400 includes a shaft 404 having a distal end and a proximal end. The shaft 404 is an elongated cylinder that is configured to pass through the passage 426 of the cannula 402 when the cannula 402 is seated in a patient. The distal end of the shaft can be passed through the cannula 402, into a workspace in the patient, to provide an operator with a view of the workspace and of other medical tools being used or otherwise within the workspace.

The shaft 404 is of sufficient stiffness to overcome friction of the cannula 402 in direction of the major axis of the shaft. That is, as the endoscope 400 is moved in and out of the passage 426, the shaft 404 is stiff enough to not deform due to friction from contacting the cannula 402. Similarly, the shaft 404 is of sufficient stiffness to overcome friction of the cannula 402 in roll about the major axis. Therefore, force applied to rotate and move the proximal end of the endoscope 400 is transmitted to the distal end of the endoscope 400. In this way, an endoscope support can move the proximal end of the endoscope 400 and predictably alter the view provided by the endoscope 400.

The endoscope 400 includes an image capturer 406 positioned at the distal end of the shaft. The image capturer 406 captures images and transmits those images to a controller or other target recipient. The image capturer 406 has a point of view (orientation of the viewpoint, which is also called the "field of view") that extends out of the distal end of the shaft 404. When the distal end of the shaft 404 is straight, this point of view is coincident with a major axis 408 of the shaft.

The image capturer 406 of the endoscope 400 includes an illuminator 410 positioned at the distal end of the shaft 404. The illuminator 410 is capable of being engaged to cast light or other energy that can be reflected and captured by the image capturer 406. (In other embodiments, the image capturer is configured to be physically separated from the energy source by the object to be sensed, and to capture energy transmitted from the energy source through or around the object to be sensed.)

The endoscope 400 includes a housing 412 positioned at the proximal end of the shaft 404. The housing 412 can house electronics, mechanical mechanisms, and other parts of the endoscope 400. The housing 412 is configured to be coupled to an endoscope support. For example, an endoscope support may have an interface that mechanically couples to the housing 412 to hold the endoscope 400. This mechanical coupling may include a sterile dressing or curtain whose use can allow for the creation of a sterile environment for operation.

The housing 412 includes a control element 414. The control element 414 can receive manipulation from an endoscope support and can cause the endoscope 400 to flex, actuate or respond. In some implementations, this control element 414 may include a data coupling through which data can pass. In some implementations, the control element 414 may include a mechanical coupling through which mechanical forces may pass. In this example, four wheels are shown, each with four posts. An endoscope support may couple to the control element with four wheels each having four recesses to receive the four posts. The endoscope support can drive the wheels of the control element 414, thereby controlling the endoscope 400.

The shaft 404 includes a flexible portion configured to flex in response to manipulation of the control element 414. The shaft 404 describes a major axis 408. The major axis 408 can be defined as an axis that passes through the middle of an area of interest of the shaft 404. Conceptually, the major axis 408 can be considered the direction along which the shaft 404 passes, with flexures of the shaft 404 being considered deviations from the direction of the shaft 404. The point of interest may change depending on the context. For example, the point of interest may be the end of the image capturer 406, the housing 412, a flexible portion of the shaft 404, a non-flexible portion of the shaft 404, or a portion of the shaft 404 in the passage 426 of a cannula.

The shaft 404 has one or more flexible portions. These portions can be flexed in directions orthogonal to the major axis 408. For example, the distal end of the endoscope 400 can be flexed to locations 416 or 418. Similarly, the proximal end of the shaft can be flexed to locations 420 or 422. In some cases, both the proximal end and the distal end of the shaft 404 can be flexed at the same time.

In some cases, the shaft 404 has one or more non-flexing portions. A non-flexing portion may be desirable, for example, in a portion that will regularly be within the passage 426 of the cannula 402, to reduce cost or complexity of the endoscope 400, or for other reasons. In some cases, the entire or substantially entire shaft 404 is flexible. An entirely flexible shaft 404 may be desirable, for example, to facilitate operations involving greater or more complex flexing of the shaft 404, to increase the types of operations that the endoscope 400 can be used for, etc.

In order to accommodate various uses during endoscopic operations, the shaft 404 can be configured to flex in one or more places at least 45 degrees or about 45 degrees (e.g., 45+/−10 degrees). However, flexures of 90 degrees or about 90 degrees (e.g., 90+/−10 degrees) may provide additional options as to view control and device placement outside of the patient.

This flexibility may be configured to be driven only the control element 414. That is, the shaft 404 may resist forces applied to the shaft 404 (e.g., a person or another tool pressing against the side of the shaft 404). To prevent pressure on the shaft 404 from back driving the control element 414, a mechanical brake may be used to lock the control element 414 when it is not receiving manipulation from an endoscope support. Notably, this behavior is different that some flexible endoscopes that are designed to follow lumens in biological or non-biological structures (e.g., drains or heating ducts). These so called "lumen following" endoscopes are often passively flexible without resisting external forces applied to their shaft. With such a configuration, they are capable of following curves in lumens. However, in some endoscopic surgeries where the endoscope 400 is preferred, they are not able to hold their shape under the forces applied to their shaft, including the force of gravity.

The cannula 402 includes a major axis 424. The major axis 424 passes through the passage 426 of the cannula 402. When the endoscope 400 is inserted into the cannula 402, the major axes 408 and 424 may or may not align. This is because the passage 426 of the cannula 402 is often wider than the shaft 404.

Also shown in FIG. 4 is another cannula 452 with a different design. A variety of cannulas may be used with the endoscopic systems and endoscopes described herein, including the cannulas 402 and 452. The cannula 452 has a larger length-to-diameter ratio compared with the cannula 402, and can contact more of shaft 404 and provide more physical constraints to the shaft 404. The cannula 452 has a major axis 464, a passage 466 through with instruments such as the shaft 404 or other instruments may pass through to access a workspace. The cannula 452 also has a shaft portion 454 on which a remote center of motion 456 about which it is designed to pivot when properly gripped and operated on its proximal end (as shown, the end farther away from the remote center of motion 456).

Figure 5:
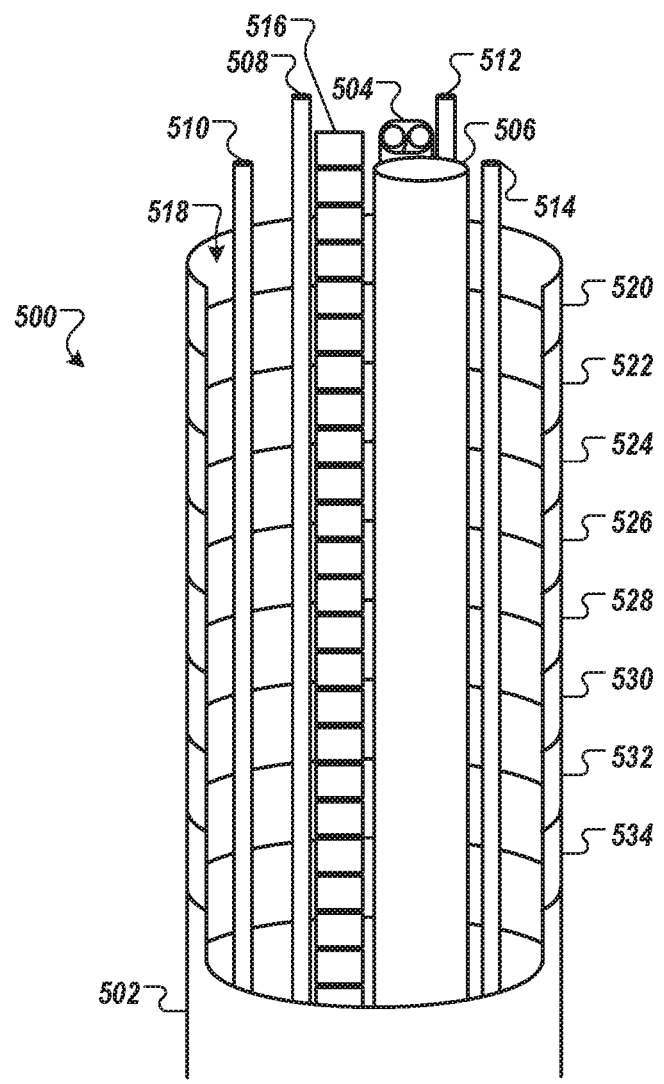
FIG. 5 shows a cut-away view of a flexible endoscope that may be used for an endoscopic procedure.

FIG. 5 shows a cut-away view of an endoscope 500 that may be used for endoscopic procedures (including for endoscopic surgery). The endoscope 500 may be used, for example, in the endoscopic systems 100, 200 and 300, or in other systems. In the view shown by FIG. 5, a shaft 502 of the endoscope 500 is cut away to expose elements of the endoscope 500 that generally pass from the proximal end of the shaft to the distal end of the shaft 502.

An activation connection 504 traverses the shaft 502 and terminates at the distal end of the shaft 502. The activation connection 504 can take a form based on the form of the illuminator in the endoscope 500. For example, the activation connection 504 may have a twisted pair of copper wires to transmit electrical signals to an LED or other light or energy source. The activation connection 504 may have a fiber optic strand to transmit light to a lens or other emitter. The activation connection 504 is configured to be switchably engaged to activate the illuminator. The switchable engagement may likewise be based on the form of the illuminator. The copper wires may close an open a circuit, or an upstream driver may emit or not emit light into the fiber optic. The copper twisted-pair may also be used as a heat sink to draw heat away from the tip and conduct it towards the proximal end.

A datalink 506 traverses the shaft 502 and allows the image capturer to transmit images. The datalink 506 can take a form based on the form of the image collector in the endoscope 500. For example, the datalink 506 may have a twisted pair of copper wires to transmit electrical signals. The datalink 506 may have a fiber optic strand to transmit light signals.

Control cables 508-514 traverse the shaft 502 to transmit flexing forces. For example, the control cables 508-514 can include cables that selectively pull on portions of the shaft 502 in response to manipulations of a control element of the endoscope 500. By using three or more cables, with four in this example, the shaft 502 can be flexed away from the major axis of the endoscope 500 in any direction.

Flexure sensors 516 are positioned in the shaft to sense the shape of the shaft. These flexure sensors 516 can sense the shape of the shaft 502 and pass that data to a controller connected to the endoscope 500. In some examples, the flexure sensor 516 can include fiber optic filaments with fiber Bragg grating (FBG). A light interrogator can uniquely measure changes in compression and elongation of the distinct gratings due to bending of the filaments. The gratings can be closely spaced such that measurable bending can be integrated along the length of the fibers to resolve the position and orientation of cross-sections of the elongate shape all the way out to the tip.

The shaft 502 forms a channel 518 configured to transmit fluid to the distal end of the shaft. For example, this channel 518 can pass gas of sufficient pressure to cool the distal end of the endoscope or to insulate the surgical area around the distal end of the endoscope. In this example, the channel 518 is formed by the inside surface of the shaft 502, and allows passage of the fluid around the other elements placed in the shaft 502. In some examples, the channel 518 can include a tube or hose that can prevent the fluid from contacting the other elements of the shaft 502 until the fluid is delivered.

The shaft 502 includes vertebrae 520-534. As previously described, vertebrae 520-534 can include movable mechanical constraints between each vertebrae 520-534. In response to tensile forces from the control cables 508-514, the vertebrae 520-534 can move within their constraints, allowing the shaft 502 to flex.

In some other examples, different configurations are possible. For example, instead of using control cables 508-514 to actively control the endoscope 500, a passively flexible endoscope may be used. In such as a case, a passively flexible endoscope having enough stiffness and damping to remain approximately straight in free-space, even after passing through a curved cannula or lumen.

Different or additional schemes may be used to sense tip orientation. For example, computer vision may be used to track tools to estimate camera orientation based on vision and kinematic information of one or more instrument tips in a view. An antagonistic arrangement of control cables within the flexible shape may be used to sense changes in tensile forces as the shape of the shaft 502 bends. The tensile forces in a given configuration can be mapped to deflections from the equilibrium pose of the shaft 502, for example.

In some uses, experimental evidence has been found that users can tolerate up to 20 degrees of reference frame misalignment without appreciable degradation of operational control. In such cases, the control cables 508-514 and/or the flexure sensor 516 may not be needed or used.

Figure 6:
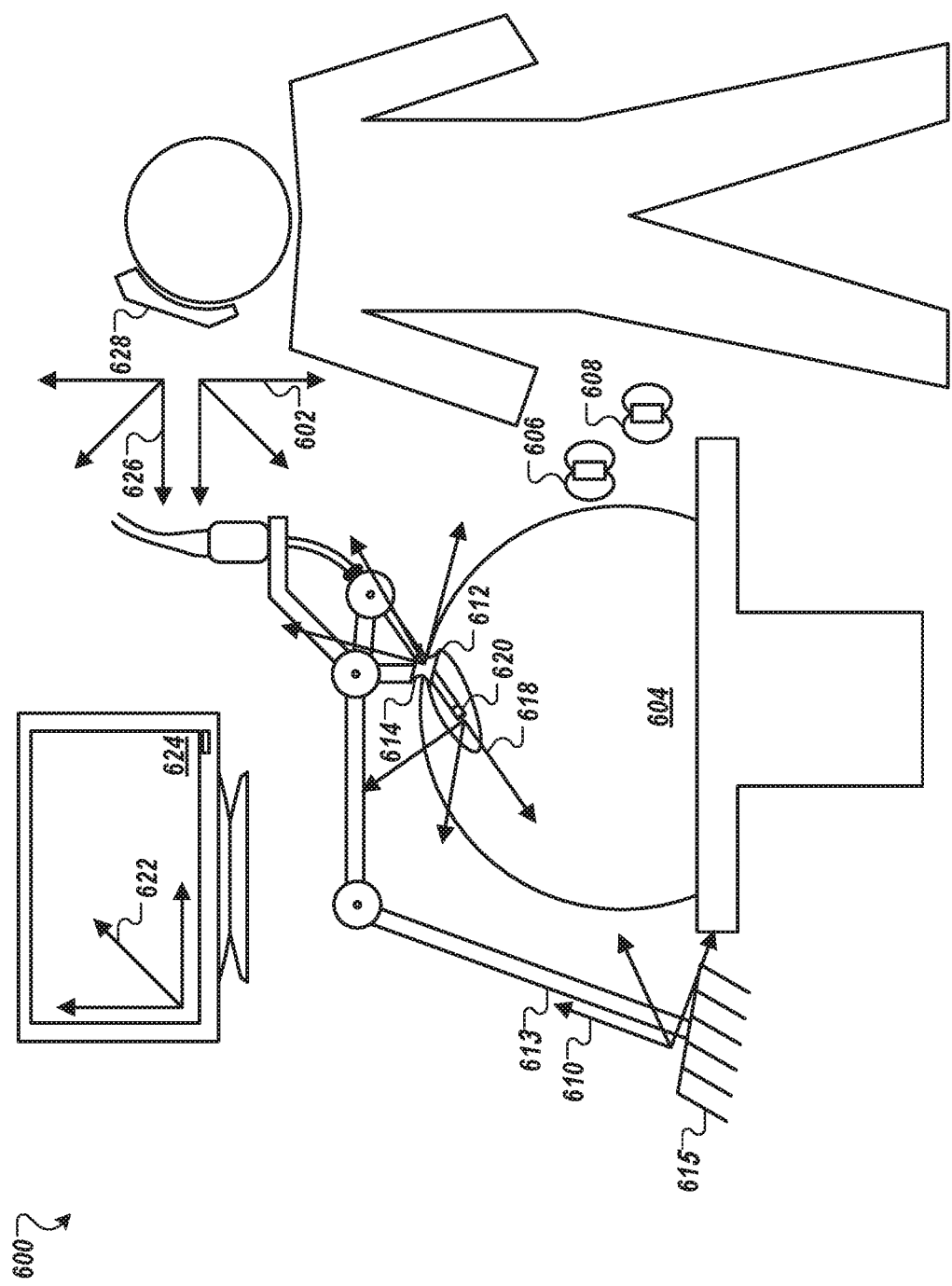
FIG. 6 shows examples of coordinate spaces that can be used in an endoscopic procedure.
Figure 7:
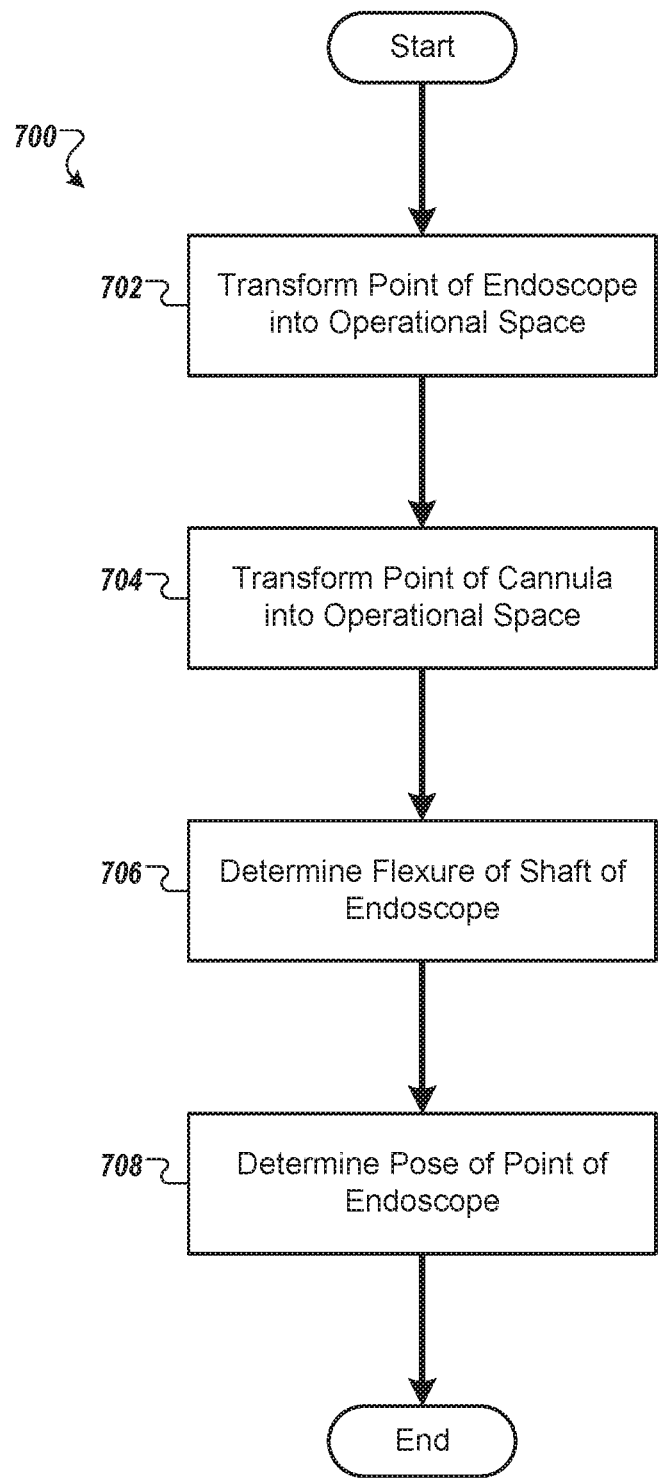
FIGS. 7-10 show example processes that may be used in controlling an endoscopic system.
Figure 8:
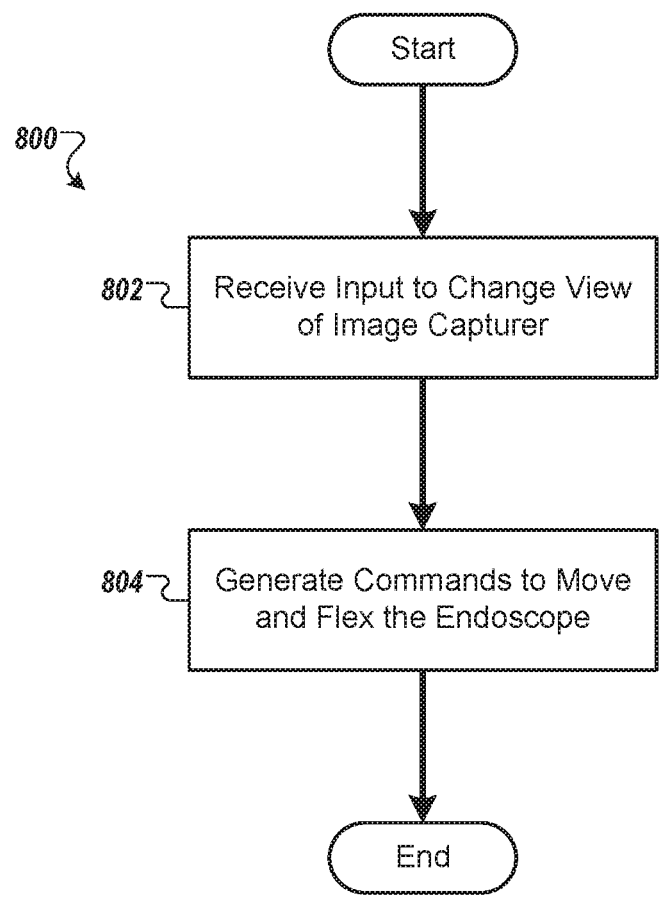
Figure 9:
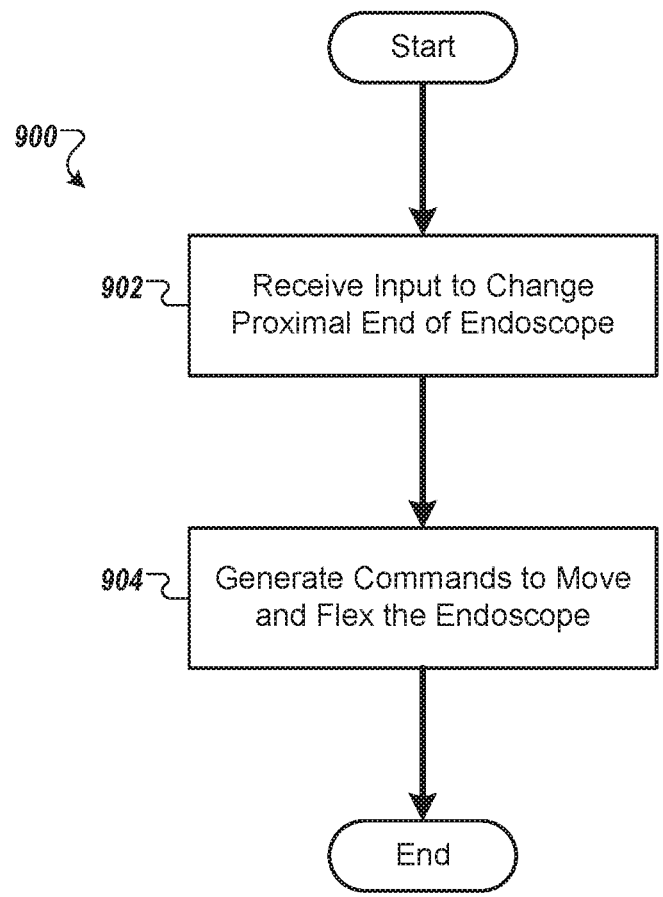
Figure 10:
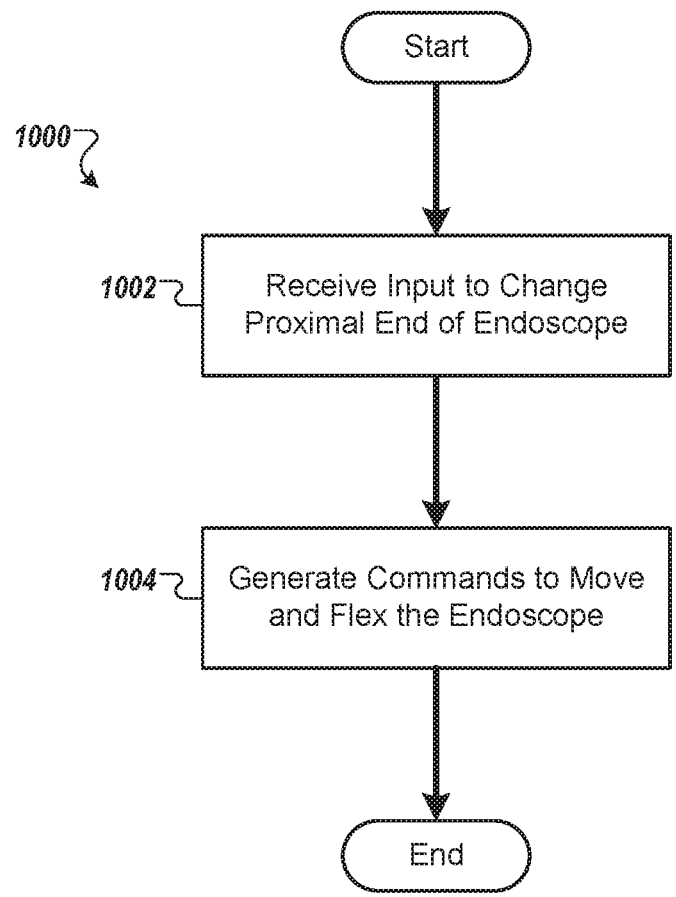

FIG. 6 shows examples of coordinate spaces that can be used in endoscopic procedures. For example, some or all of these coordinate spaces may be used analogously with any or all of the endoscopic systems 100, 200, 300 and the endoscopes 400, 500. An endoscopic system 600 can reference points of various components based on one or more coordinate spaces.

A procedure space 602 is shown with an axis pointing toward a point within a patient 604. In some implementations, a Z-axis of the procedure space 602 is the axis pointing toward a point within the patient 604. This configuration may be useful, for example, to aid in calculations and human recognition of an endoscopic surgery. Moving 'into' or 'toward' the patient is associated with the Z-axis, which is often associated with moving 'into' or 'toward' a viewport or destination in other contexts that an operator may be familiar with.

Some elements of the endoscopic system 600 may be tracked in the procedure space 602. That is, sensors data that reports the location of these elements may be calculated to find points in the procedure space 602. For example, input device 606 and 608 may be motion tracked in the procedure space 602.

A support space 610 is shown with an axis aligned with a link of a robotic arm 613 (also "manipulator" or "robotic manipulator") that is mechanically grounded (as indicated by the link's connection to a mechanical ground 615). In some implementations, a Z-axis of the support space 610 is the axis aligned with the link. In another example with two or more robotic arms, each arm may have its own associated space.

Links of the robotic arm may be tracked in the support space 610. For example, the robotic arm may have sensors between each link. These sensors may report the angle between the links. From these angle readings, points along the robotic arm may be found in the support space 610.

A cannula space 612 is shown with an origin location and origin orientation relative to a cannula 614. For example, the origin may be at the center point of a passage going through the cannula 614, with a Z-axis along the major axis of the cannula.

An endoscope space 618 is shown with an origin location and origin orientation relative to an endoscope 620. In this case, the origin location is tied to the tip or image capturer of the endoscope 620 and represents the viewpoint of the endoscope 620. As is often a convention with coordinate spaces for viewpoints, the Z-axis of the endoscope space 618 may have a Z-axis that is normal to the viewplane of the endoscope. The Y-axis may point in an up direction in the viewplane, and a X-axis may point in a left direction in the viewplane. Different or additional endoscope spaces may be used. For example, an endoscope space centered on the proximal end of the endoscope 620 may be useful for calculating a movement path of the distal end of the endoscope. In another example, an endoscope space 618 near the middle of the shaft of the endoscope 620 may be useful for ensuring that the shaft of the endoscope 620 is not being moved along a path that will collide with the cannula 614.

A display space 622 is shown with an origin location and origin orientation relative to a display 624. In this case, the origin location is tied to a lower-left corner of the display with a Z-axis that is normal to the viewplane of the display 624. With such a configuration, the view of the endoscope 620 may be faithfully replicated on the display 624.

A stereoscopic space 626 is shown with an origin location and origin orientation relative to a stereoscopic display 628. In this case, the origin location is tied to a lower-left corner of the display with a Z-axis that is normal to the viewplane of the stereoscopic display 628. With such a configuration, the view of the endoscope 620 may be faithfully replicated on the stereoscopic display 628.

A processor or control system (e.g., the controller 114 of endoscopic system 100, or the controllers of the other endoscopic systems disclosed herein) can transform points in one coordinate space into corresponding points in another coordinate space. For example, in a 3D coordinate space, points can be defined as a vector of three values (i.e. $[X_1,Y_1,Z_1]$). When two coordinate spaces overlap, that same point can be expressed in another coordinate space by another vector (i.e. $[X_2,Y_2,Z_2]$). To transform from $[X_1,Y_1,Z_1]$ to $[X_2,Y_2,Z_2]$, the processor can perform a function called a coordinate space transform. This coordinate space transform often involves multiplying the vector of the first point with a transform matrix to produce the vector in the second coordinate space. As will be understood, orientations may also be represented as a vector of three values that may be similarly transformed.

In order to perform these transforms, the data defining the transform between various coordinate spaces may be recorded and used as needed. For example, to transform a point in the support space 610 to a point in the procedure space 602, a support-to-surgical transform matrix may be used. In some cases, these transforms may be chained. To transform a point in the endoscope space to the surgical space, the point can be multiplied by an endoscope-to-support transform matrix, and then by a support-to-surgical transform matrix.

These transform matrices may be updated as the elements of the endoscopic system 600 move. For example, as an endoscope moves (including by flexing), its position relative to other elements changes. In response, the processor can continually update the values of transform matrices associated with the endoscope. By doing so, the processor may transform points into and out of the endoscope space even as the endoscope is moving or flexing.

In this example, the coordinate spaces are described as Cartesian coordinate spaces. However, other coordinate spaces may be used. For example, polar coordinate spaces may be useful for some mechanical elements that have rotational movements, and projection spaces may be useful for augmenting a stereoscopic view.

FIGS. 7-10 show example processes 700, 800, 900, and 1000 that may be used in controlling an endoscopic system such as any of the endoscopic systems described herein. For clarity, these processes will be described with reference to the endoscopic system 100 of FIG. 1. However, other systems may be used to perform these or other similar processes. For example, the endoscopic systems 200, 300 or the endoscopes 400, 500 may be used to perform these processes 700, 800, 900, 1000 or other similar processes.

In general, the processes 700, 800, 900, and 1000 may be used to control elements of endoscopic systems in which automated sensing and control of mechanical elements are used to assist the activity. Various schemes for sensing and control are possible, depending in part on the capabilities of the elements of the system used to perform the processes 700, 800, 900, and 1000.

Described now in connection with the endoscopic system 100, the process 700 describes the determination of a pose of a spatial frame originating at a point of the flexible endoscope 106, where the flexible endoscope 106 is held by the endoscope support 112 and passes through the cannula 108 into the workspace 110. In general, the pose of a point includes both the location and the orientation of the spatial frame originating at the point within a particular space. Here, the pose of a point of the flexible endoscope 106 is found in a procedure space. The process 700 may be useful, for example, to determine where a point of the flexible endoscope 106 is in relation to other elements of the endoscopic system 100. When determining a path to move the flexible endoscope 106, the controller 114 may first be configured to determine where the flexible endoscope 106 is, and the process 700 may be used for this task. Further, teleoperation of instruments used with the flexible endoscope 106 (such as surgical instruments in a surgical procedure) may involve mapping workspaces of the instruments into the orientation frame of the flexible endoscope's 106 tip. To perform this mapping, the orientation of the pose of the tip of the flexible endoscope 106 may be used.

A first location of a point of the endoscope is transformed in 702 into the procedure space. For example, the controller 114 may be configured to use the base of the shaft of the flexible endoscope 106, where the shaft is rigidly held by the endoscope support 112, as the origin of an endoscopic space. To transform this origin point into a point in the procedure space, the controller 114 may apply an endoscope-to-endoscope support transform matrix and an endoscope support-to-surgical transform matrix. This application can result in the controller 114 determining a location and orientation (i.e. pose) of the origin of the endoscope space in the procedure space.

A second location of a point of the cannula 108 is transformed in 704 into surgical space. For example, the controller 141 may be configured to use a point in the center of the cannula 108 as the origin of the endoscopic space. To transform this point to a point in the procedure space, the controller 114 may apply a cannula-to-cannula support transform matrix and a cannula support-to-surgical space transform matrix. This application can result in the controller 114 determining a location and orientation (i.e. pose) of the origin of the cannula space in the procedure space.

A flexure of the shaft of the endoscope is determined in 706. For example, the controller 114 can sense and/or calculate the shape of the flexible endoscope 106.

To sense the flexure of the flexible endoscope 106, the controller 114 can be configured to receive readings from a flexure sensor within the shaft of the flexible endoscope 106. In some configurations, this flexure sensor may provide the controller 114 with the full shape of the shaft of the flexible endoscope 106. However, in some configurations, the flexure sensor may only provide partial information about the shape of the shaft. That is, the flexure sensor may provide information about the total deviation from the major axis of the flexible endoscope 106, but not where in the shaft that flexure starts or in what direction.

In cases of no or partial sensed information, the controller 114 can calculate the shape of the flexible endoscope 106 based on a number of constraints. The pose of the origin of the endoscope space may be used for one constraint as this origin is set to be in a fixed location in the flexible endoscope 106. For another constraint, the pose of the cannula space may be used as the shaft of the flexible endoscope 106 passes through the cannula 108.

Additional constraints may be used based on the partial sensed information. In one example, if the partial information is that the distal end of shaft flexes a particular distance from the major axis, the controller 114 can generate a mathematical constraint that the distal end of the flexible endoscope 106 be that distance from the major axis.

A pose of a point of the endoscope is determined in 708. For example, the controller 114 can use the pose of the origin of the endoscope space, the pose of the origin of the cannula space, and the flexure of the shaft of the flexible endoscope 106 as constraints to solve for the location of a point of interest in the flexible endoscope 106.

This point of interest may be any point of the flexible endoscope 106, depending on the calculation involved. Additionally, the controller 114 can be configured to avoid contacting the cannula 108 with the flexible endoscope 106. In order to do so, the controller 114 may calculate the poses of other points along the shaft of the endoscope 106 near the cannula 108 to ensure any commands for movement of the flexible endoscope 106 (including any changes in flexure) do not cause contact with the cannula 108. In a similar fashion, other movements may involve the determination of the pose of other points. Commands to move the proximal end of the flexible endoscope 106 may involve determining the poses of a plurality of points of the flexible endoscope 106 outside of the cannula 108, for example.

Described now in conjunction with the endoscopic system 100, the process 800 describes the movement of the flexible endoscope 106 to change the view of the image capturer 130. While some view changes only involve flexing the shaft of the flexible endoscope 106, many view changes also involve moving the image capturer 130 into or out of the workspace 110 along the Z-axis of the procedure space. To do so, the endoscope support 112 actuates to push or pull the flexible endoscope 106 through the cannula 108 while the shaft flexes.

Generating commands to actuate the endoscope support 112 is complicated by the flexible nature of the flexible endoscope 106 when the flexible endoscope 106 is not otherwise held rigid. In such a case, the commands generally cannot actuate the endoscope support 112 merely in the Z-axis of the procedure space. Instead, the commands also account for orientation changes of the proximal end of the flexible endoscope 106, the flexed portion of the shaft of the endoscope 106 that passes through the cannula 108, and commands to change the flexure of the flexible endoscope 106 as it moves through the cannula 108.

In order to generate these commands, the controller 114 can use the process 800 to determine the poses of a plurality of points of the endoscope as part of performing the process 800.

Input is received in 802 to change the view of the image capturer 130. For example, the operator 102 may manipulate the input devices 132 and 134 to indicate a desire to zoom, pan, tilt, and rotate, etc., the view presented in the stereoscopic display 120 or the monitor 118. These manipulations may be tracked by the endoscopic system 100 and passed to the controller 114.

Commands are generated in 804 to move and flex the endoscope 106. For example, the controller 114 can generate commands for the endoscope support 112 to actuate and move the endoscope support 112 and/or for the cannula support 116 to actuate and move the cannula support 116. At the same time, the controller 114 can also generate commands to change the flexure of the shaft of the flexible endoscope 106. By combining these two articulations, the controller 114 can generate commands that will change the point of view of the image capturer 130 as the operator 102 indicated.

To generate these commands, the controller 114 map view reference commands to endoscope tip commands, and then map the endoscope tip commands to endoscope support and/or cannula support commands. For example, an input from the user may indicate a particular change in the view reference. The controller 114 can map this change in the view reference to a change in the endoscope tip pose. Next, the controller 114 can map this change in endoscope tip pose into changes in the endoscope support 112 and/or for the cannula support 116.

The controller 114 can also account for other elements of the endoscopic system 100 when generating these commands. For example, the location of the cannula 108 and other equipment may be tracked by the controller 114, which may ensure that the commands to change the view do not cause the flexible endoscope 106 or endoscope support 112 to collide with the other elements. In another example, the backend of the flexible endoscope 106 may be moved to avoid collisions with other manipulators or instruments or to preserve the working space of a clinician or other operator.

In some implementations, the cannula 108 may have one or more curved passages instead of one generally straight passage. In such cases, a flexible endoscope 106 may be used. In these cases, the controller 114 can generate commands that move the flexible portion of the shaft through the curved passage along the path of the curved passage. In these cases, the endoscope support 112 may not need to have a degree of freedom for changing the orientation of the insertion axis and the endoscope support 112 moves the flexible endoscope 106 through a curved passage of the cannula.

Described now in conjunction with the endoscopic system 100, the process 900 describes the movement of the proximal end of the flexible endoscope 106 while maintaining the view of the image capturer 130. This movement, sometimes called a nullspace movement, can allow for greater freedom to arrange the elements of the endoscopic system 100, especially in the area directly around the patient 104. By moving the endoscope support 112 without changing the view of the image capturer 130, the operator 102 is able to reposition other equipment or themselves into more preferred positions for performing the procedure, or more ergonomic positions.

In general, nullspace move are moves of a manipulator where one or more Cartesian degrees of freedom of the endpoint are held stationary in the surgical space while one or more proximal degrees of freedom are moved. In the case of the endoscopic system 100, the flexible endoscope 106 and endoscope support 112 can combine to provide more than three degrees of freedom. By doing so, they provide redundant degrees of freedom that can be utilized for these kinds of nullspace movements.

In order to generate these commands, the controller 114 can use the process 700 to determine the poses of a plurality of points of the endoscope as part of performing the process 900.

Input is received 902 to move the proximal end of the endoscope 106. For example, the operator 102 may manipulate the input devices 132 and 134 to indicate a desire to the proximal end of the flexible endoscope 106. These manipulations may be tracked by the endoscopic system 100 and passed to the controller 114.

Additionally or alternatively, the operator 102 can push on the proximal end of the flexible endoscope 106, the endoscope support 112, or another element of the endoscopic system 100. This may be provided, for example, when using an endoscope controller that is configured to allow proximal movement of the endoscope that is decoupled from movement of the distal portion. Sensors in the flexible endoscope 106, the endoscope support 112, or elsewhere can sense this backdriving force and transmit to the controller 114.

The flexible endoscope 106 can utilize a hybrid nullspace and proximal float control mode in which the position controller of the proximal degrees of freedom regulates commanded position to track actual position while the position controller for the distal degrees of freedom are commands to keep the endoscope tip stationary. Some traditional endoscope control interfaces have a button at the top of the arm that floats the pitch, yaw, insertion, and roll degrees of freedom together so that the user can directly manipulate the backend to affect the position and orientation of the endoscope tip. A variation on this control interface can allow the user to selectively choose between controlling the endoscope tip versus adjusting the pose of the endoscope backend.

Commands are generated in 904 to move and flex the endoscope. For example, For example, the controller 114 can generate commands for the endoscope support 112 to actuate and move the endoscope support 112. At the same time, the controller 114 can also generate commands to change the flexure of the shaft of the flexible endoscope 106. By combining these two articulations, the controller 114 can generate commands that will change the shape of the shaft outside of the cannula 108 and the location of the proximal end of the flexible endoscope 106 without changing the shape of the shaft within the workspace 110 and cannula 108. In this way, the proximal end of the flexible endoscope 106 can be moved without changing the view of the image capturer 130.

The controller 114 can also account for other elements of the endoscopic system 100 when generating these commands. For example, the location of the cannula 108 and other equipment may be tracked by the controller 114, which may ensure that the commands to change the proximal end of the flexible endoscope 106 do not cause the flexible endoscope 106 or endoscope support 112 to collide with the other elements.

Described now in conjunction with the endoscopic system 100, the processes 1000 describes the movement of the cannula 108 with the flexible endoscope 106 inserted. This movement may be used when beginning or ending an endoscopic procedure. Specifically, if an endoscopic procedure becomes problematic and the operator determines that an emergency cancellation is necessary, the process 1000 can be used to remove both the cannula and the endoscope in a single action. Additionally, the process 1000 could be used to adjust the proximal end of the flexible endoscope 106 and the cannula 108 as a nullspace movement while keeping the image capturer 130 steady.

Input is received 1002 to move the cannula 108. For example, the operator 102 may manipulate the input devices 132 and 134 to indicate a desire to the cannula 108. These manipulations may be tracked by the endoscopic system 100 and passed to the controller 114.

Commands are generated to move 1004 with the endoscope with the cannula. For example, the controller 114 can generate commands for the endoscope support 112 to actuate, commands for the cannula support 116 to actuate, and commands to change the flexure of the shaft of the flexible endoscope 106. By combining these three articulations, the controller 114 can generate commands that will change the location of the cannula 108 and the proximal end of the flexible endoscope 106. Depending on the input, the commands may also maintain the view of the image capturer 130, or not.

The controller 114 can also account for other elements of the endoscopic system 100 when generating these commands. For example, the location of other equipment may be tracked by the controller 114, which may ensure that the commands to change the location of the cannula 108 do not cause the flexible endoscope 106 or endoscope support 112 to collide with the other elements.

Thus, as described in conjunction in FIGS. 7-10, and also in conjunction with FIGS. 1, 6, and the other figures, various embodiments utilize a method of controlling a field of view of an endoscope. The method comprises determining a pose of the field of view using a first location and a second location, and controlling the pose of the field of view by moving the first portion, the second portion, or both the first and second portions. The first location is of a first portion of the endoscope and the second location is of a second portion of the endoscope. The endoscope comprises a flexible portion disposed between the first portion and the second portion. The first and second locations are defined by a configuration, relative to the endoscope, of an endoscope support and a cannula. The endoscope support configured to support the endoscope. The shaft of the endoscope is configured to extend through the cannula.

In some embodiments, the pose of the field of view is determined by determining a pose of a distal end of the shaft based on the first and second locations, by determining a flexure of the shaft using the first and second locations, or the like.

In some embodiments, controlling the pose of the field of view comprises moving the first portion by moving the endoscope support, moving the second portion by moving the cannula, rolling the field of view by rotating the endoscope support and causing rotation of the first portion, changing a yaw or a pitch of the field of view by changing a yaw or a pitch of the cannula, moving the first portion and the second portion, any combination of the foregoing, or the like.

In some embodiments, moving the first portion and the second portion comprises moving the first portion in accordance with a first movement and moving the second portion in accordance with a second movement, where the first and second movements performed separately would roll the field of view, and where the first and second movements performed in combination would not roll the field of view.

In some embodiments, moving the first portion and the second portion comprises moving the endoscope support and moving the cannula.

In some embodiments, the method further comprises controlling the pose of the field of view by actively driving a change in a flexure of the shaft.

In some embodiments, the method further comprises receiving a command to move a proximal portion of the endoscope without changing a pose of a distal end of the shaft, determining a movement of at least one of the endoscope support and the cannula, where the movement would move the proximal portion of the endoscope without changing the pose of the distal end by moving at least one of the first and second portions, and driving motion of the at least one of the endoscope support and the cannula in accordance with the movement.

In some embodiments, controlling the pose of the field of view comprises moving at least one of the first portion and the second portion in response to: determining that a deflection the endoscope support is past a deflection criterion, determining that a force applied to the endoscope is past a force criterion, determining a combination thereof, or the like.

Figure 11:
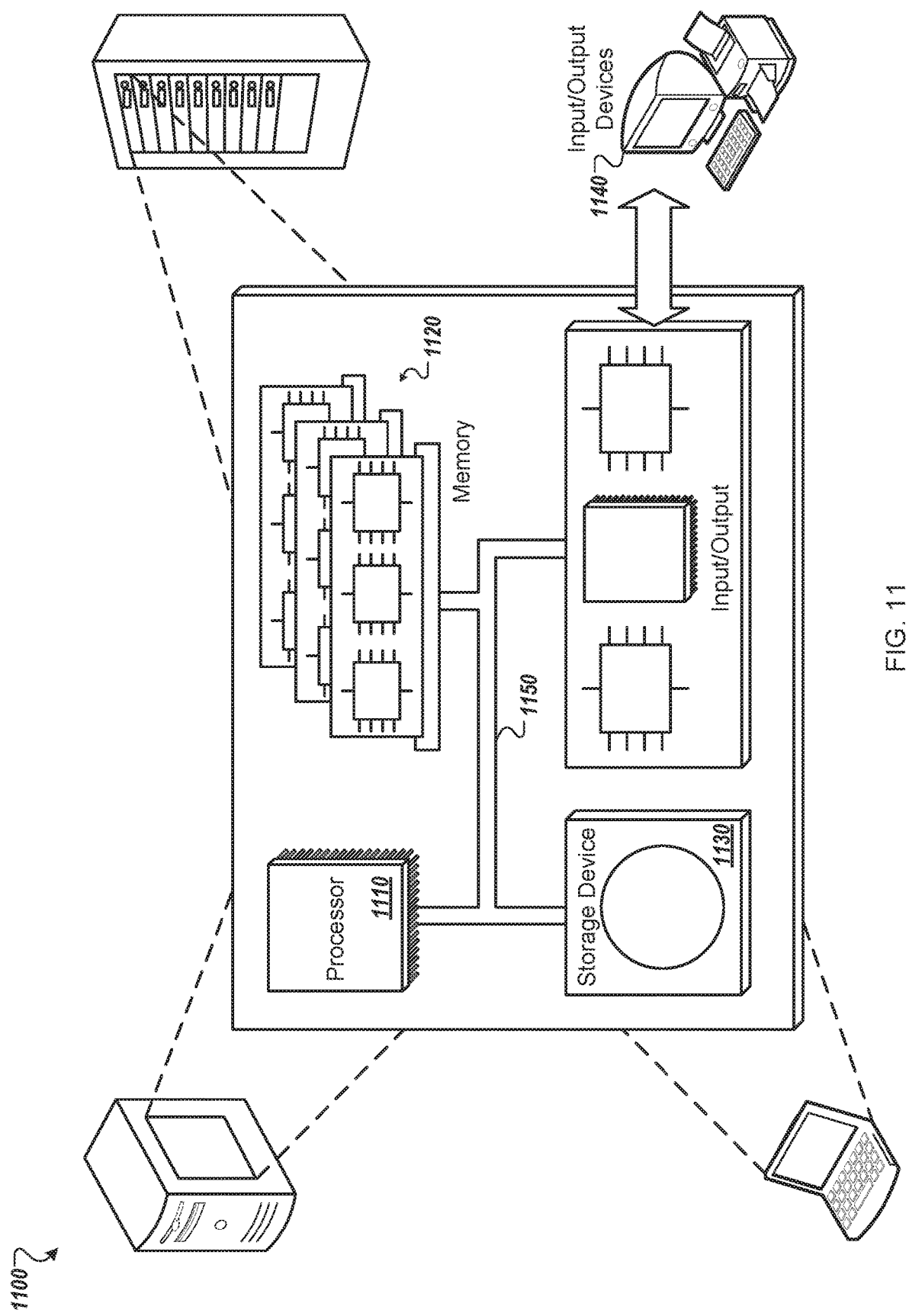
FIG. 11 is a schematic diagram that shows an example of a computing system.

FIG. 11 is a schematic diagram that shows an example of a computing system 1100 that may be used to implement, or that may comprise, the controller 114 or any other controller described herein. The computing system 1100 can be used for some or all of the operations described previously, according to some implementations. The computing system 1100 includes a processor 1110, a memory 1120, a storage device 1130, and an input/output device 1140. Each of the processor 1110, the memory 1120, the storage device 1130, and the input/output device 1140 are interconnected using a system bus 1150. The processor 1110 is capable of processing instructions for execution within the computing system 1100. In some implementations, the processor 1110 is a single-threaded processor. In some implementations, the processor 1110 is a multi-threaded processor. The processor 1110 is capable of processing instructions stored in the memory 1120 or on the storage device 1130 to display graphical information for a user interface on the input/output device 1140.

The memory 1120 stores information within the computing system 1100. In some implementations, the memory 1120 is a computer-readable medium. In some implementations, the memory 1120 is a volatile memory unit. In some implementations, the memory 1120 is a non-volatile memory unit.

The storage device 1130 is capable of providing mass storage for the computing system 1100. In some implementations, the storage device 1130 is a computer-readable medium. In various different implementations, the storage device 1130 may be a floppy disk device, a hard disk device, an optical disk device, or a tape device.

The input/output device 1140 provides input/output operations for the computing system 1100. In some implementations, the input/output device 1140 includes a keyboard and/or pointing device. In some implementations, the input/output device 1140 includes a display unit for displaying graphical user interfaces.

Some features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM (erasable programmable read-only memory), EEPROM (electrically erasable programmable read-only memory), and flash memory devices; magnetic disks such as internal hard disks and removable disks; magneto-optical disks; and CD-ROM (compact disc read-only memory) and DVD-ROM (digital versatile disc read-only memory) disks. The processor and the memory can be supplemented by, or incorporated in, ASICs (application-specific integrated circuits).

To provide for interaction with a user, some features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

Some features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN (local area network), a WAN (wide area network), and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. An endoscopic system comprising:
    an endoscope configured to be supported by an endoscope support, the endoscope comprising:
        a shaft configured to extend through a cannula, the shaft comprising a flexible portion disposed between a first portion of the endoscope and a second portion of the endoscope, wherein the flexible portion is configured to be disposed between the endoscope support and the cannula, and wherein the flexible portion is configured to flex in response to relative movement of the endoscope support and the cannula, and
        an image capturer configured to capture an image from a field of view; and a controller communicably coupled to the endoscope, the controller configured to:
    determine a first location of the first portion of the endoscope and a second location of the second portion of the endoscope, and
    determine a pose of the field of view using the first location of the first portion of the endoscope and the second location of the second portion of the endoscope,
    wherein the flexible portion is disposed between the first portion and the second portion, and
    wherein the pose of the field of view comprises a position and an orientation of the field of view.

2. The endoscopic system of claim 1, wherein the controller is configured to determine the pose of the field of view using the first location and the second location by:
    determining a pose of a distal end of the shaft based on the first and second locations, or
    determining a flexure of the shaft using the first and second locations, or
    using the first location, the second location, and the flexure of the shaft.

3. The endoscopic system of claim 1, wherein the controller is further configured to:
    control the pose of the field of view by moving at least one portion of the endoscope selected from the group consisting of: the first portion and the second portion.

4. The endoscopic system of claim 3, wherein
    the controller moves the first portion by moving the endoscope support; or
    the controller moves the second portion by moving the cannula.

5. The endoscopic system of claim 1, wherein the controller is further configured to roll the field of view by:
    rotating the endoscope support and causing rotation of the first portion, or
    rotating a cannula support configured to support the cannula, and causing rotation of the second portion.

6. The endoscopic system of claim 1, wherein the controller is further configured to:
    change a yaw or a pitch of the field of view by changing a yaw or a pitch of the cannula.

7. The endoscopic system of claim 1, wherein the controller is further configured to:
    control the pose of the field of view by:
        moving the endoscope support to move the first portion in accordance with a first movement; and
        moving the cannula to move the second portion in accordance with a second movement, wherein the first and second movements, if performed separately, rolls the field of view, and wherein the first and second movements, if performed in combination, does not roll the field of view.

8. The endoscopic system of claim 1, wherein
    the controller is further configured to:
        control the pose of the field of view by moving the first portion and the second portion; and
    the controller moves the first portion by moving the endoscope support, and wherein the controller moves the second portion by moving the cannula.

9. The endoscopic system of claim 1, wherein the controller is further configured to:
    control the pose of the field of view by actively driving a change in a flexure of the shaft.

10. The endoscopic system of claim 9, wherein the controller actively drives the change in the flexure of the shaft by controlling a tension in a drive cable extending through the shaft.

11. The endoscopic system of claim 1, wherein the controller is further configured to:
receive a command to move a proximal portion of the endoscope without changing a pose of a distal end of the shaft;
determine a movement of at least one component selected from group consisting of: the endoscope support and the cannula, wherein the movement would move the proximal portion of the endoscope without changing the pose of the distal end by moving at least one portion of the endoscope selected from the group consisting of: the first portion and the second portion; and
drive motion of at least one component selected from the group consisting of: the endoscope support and the cannula in accordance with the movement.

12. The endoscopic system of claim 1, further comprising:
the endoscope support, wherein the endoscope support comprises a mechanical brake configured to prevent the endoscope from moving.

13. The endoscopic system of claim 1, further comprising the endoscope support, wherein the endoscope support comprises a sensor configured to sense:
a deflection of a joint of the endoscope support, or
a deflection of a link of the endoscope support, or
a force applied to the endoscope support.

14. The endoscopic system of claim 13, wherein the controller is further configured to move the endoscope support in response to:
determining that the deflection of the joint is past a joint deflection criterion; or
determining that the deflection of the link is past a link deflection criterion; or
determining that the force applied is past a force criterion.

15. A method of controlling a field of view of an endoscope, the method comprising:
determining a pose of the field of view using a first location and a second location, the first location being of a first portion of the endoscope and the second location being of a second portion of the endoscope, wherein the endoscope comprises a flexible portion disposed between the first portion and the second portion, wherein the pose comprises a position and an orientation of the field of view of the endoscope, and wherein a shaft of the endoscope is configured to extend through a cannula; and
controlling the pose of the field of view by moving at least one portion of the endoscope selected from the group consisting of: the first portion of the endoscope and the second portion of the endoscope by causing movement of at least one component selected from the group consisting of: the cannula and an endoscope support configured to support the endoscope and the cannula, wherein the flexible portion is configured to be disposed between the endoscope support and the cannula and is configured to flex in response to relative movement of the endoscope support and the cannula during operation.

16. The method of claim 15, wherein determining the pose of the field of view using the first location and the second location comprises:
determining a pose of a distal end of the shaft based on the first and second locations; or
determining a flexure of the shaft using the first and second locations.

17. The method of claim 15, wherein controlling the pose of the field of view comprises:
moving the first portion by moving the endoscope support; or
moving the second portion by moving the cannula.

18. The method of claim 15, wherein controlling the pose of the field of view comprises:
moving the endoscope support to move the first portion in accordance with a first movement; and
moving the cannula to move the second portion in accordance with a second movement, wherein the first and second movements, if performed separately, rolls the field of view, and wherein the first and second movements, if performed in combination, does not roll the field of view.

19. The method of claim 15 wherein moving the pose of the field of view comprises:
moving the endoscope support and moving the cannula.

20. The method of claim 15, wherein the at least one component of the endoscope is at least one first component of the endoscope, the method further comprising:
receiving a command to move a proximal portion of the endoscope without changing a pose of a distal end of the shaft;
determining a movement of at least one second component selected from the group consisting of: the endoscope support and the cannula, wherein the movement would move the proximal portion of the endoscope without changing the pose of the distal end by moving at least one fourth portion of the endoscope selected from the group consisting of: the first portion and the second portion; and
driving motion of the at least one second component in accordance with the movement.

21. The method of claim 15, wherein controlling the pose of the field of view comprises moving at least one fourth portion selected from the group consisting of: the first portion and the second portion in response to:
determining that a deflection the endoscope support is past a deflection criterion; or
determining that a force applied to the endoscope is past a force criterion.

22. A non-transitory machine-readable medium comprising a plurality of machine-readable instructions which when executed by one or more hardware processors are adapted to cause the one or more hardware processors to perform a method of controlling a field of view of an endoscope, the method comprising:
determining a pose of the field of view using a first location and a second location, the first location being of a first portion of the endoscope and the second location being of a second portion of the endoscope, wherein the endoscope comprises a flexible portion disposed between the first portion and the second portion, wherein the pose comprises a position and an orientation of the field of view of the endoscope, and wherein a shaft of the endoscope is configured to extend through a cannula; and
controlling the pose of the field of view by moving at least one portion of the endoscope selected from the group consisting of: the first portion of the endoscope and the second portion of the endoscope by causing movement of at least one component selected from the group consisting of: the cannula and an endoscope support configured to support the endoscope and the cannula, wherein the flexible portion is configured to be disposed between the endoscope support and the cannula and is configured to flex in response to relative movement of the endoscope support and the cannula during operation.

23. The non-transitory machine-readable medium of claim 22, wherein controlling the pose of the field of view comprises:

moving the first portion by moving the endoscope support; or moving the second portion by moving the cannula.

24. The non-transitory machine-readable medium of claim 22, wherein controlling the pose of the field of view comprises:

moving the endoscope support to move the first portion in accordance with a first movement; and moving the cannula to move the second portion in accordance with a second movement, wherein the first and second movements, if performed separately, rolls the field of view, and wherein the first and second movements, if performed in combination, does not roll the field of view.

\* \* \* \* \*